US009386985B2

(12) United States Patent
Koch, Jr. et al.

(10) Patent No.: US 9,386,985 B2
(45) Date of Patent: Jul. 12, 2016

(54) SURGICAL CUTTING INSTRUMENT

(71) Applicant: Ethicon Endo-Surgery, Inc., Cincinnati, OH (US)

(72) Inventors: Robert L. Koch, Jr., Cincinnati, OH (US); Andrew T. Beckman, Cincinnati, OH (US); Eric W. Thompson, Pleasant Plain, OH (US); Rachel M. Clair, Lebanon, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 777 days.

(21) Appl. No.: 13/651,589

(22) Filed: Oct. 15, 2012

(65) Prior Publication Data

US 2014/0103093 A1    Apr. 17, 2014

(51) Int. Cl.
*A61B 17/068* (2006.01)
*A61B 17/3207* (2006.01)
*A61B 17/072* (2006.01)

(52) U.S. Cl.
CPC ..... *A61B 17/07207* (2013.01); *A61B 17/32075* (2013.01); *A61B 2017/07285* (2013.01)

(58) Field of Classification Search
CPC ................... A61B 17/068; A61B 2017/07285
USPC ...................................................... 227/180.1
See application file for complete search history.

(56) References Cited

U.S. PATENT DOCUMENTS

| 4,873,977 A | 10/1989 | Avant et al. |
| 4,893,622 A | 1/1990 | Green et al. |
| 5,465,894 A | 11/1995 | Clark et al. |
| 5,465,895 A | 11/1995 | Knodel et al. |
| 5,507,426 A | 4/1996 | Young et al. |
| 5,752,644 A | 5/1998 | Bolanos et al. |
| 5,758,814 A | 6/1998 | Gallagher et al. |
| 5,911,353 A | 6/1999 | Bolanos et al. |
| 6,102,271 A | 8/2000 | Longo et al. |
| 6,126,058 A | 10/2000 | Adams et al. |
| 6,179,195 B1 | 1/2001 | Adams et al. |
| 6,193,129 B1 | 2/2001 | Bittner et al. |
| 6,241,140 B1 | 6/2001 | Adams et al. |
| 6,264,086 B1 | 7/2001 | McGuckin, Jr. |
| 6,264,087 B1 | 7/2001 | Whitman |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

International Search Report for PCT/US2013/064195, Apr. 7, 2014 (6 pages).

(Continued)

*Primary Examiner* — Thanh Truong
*Assistant Examiner* — Patrick Fry

(57) ABSTRACT

A surgical cutting instrument includes a first jaw member, a second jaw member movably supported relative to the first jaw member for selective movement between an open position and a closed position to clamp tissue therebetween upon application of a closing motion thereto, and a cutting member comprising a tissue cutting edge to cut the tissue clamped between the first jaw member and the second jaw member upon application of a retraction motion to the cutting member.

18 Claims, 24 Drawing Sheets

(56) References Cited

U.S. PATENT DOCUMENTS

| | | | |
|---|---|---|---|
| 6,315,184 B1 | 11/2001 | Whitman |
| 6,343,731 B1 | 2/2002 | Adams et al. |
| 6,478,210 B2 | 11/2002 | Adams et al. |
| 6,488,197 B1 | 12/2002 | Whitman |
| 6,491,201 B1 | 12/2002 | Whitman |
| 6,505,768 B2 | 1/2003 | Whitman |
| 6,601,749 B2 | 8/2003 | Sullivan et al. |
| 6,629,630 B2 | 10/2003 | Adams |
| 6,681,979 B2 | 1/2004 | Whitman |
| 6,695,199 B2 | 2/2004 | Whitman |
| 6,698,643 B2 | 3/2004 | Whitman |
| 6,805,273 B2 | 10/2004 | Bilotti et al. |
| 6,820,791 B2 | 11/2004 | Adams |
| 6,827,246 B2 | 12/2004 | Sullivan et al. |
| RE38,708 E | 3/2005 | Bolanos et al. |
| 6,905,057 B2 | 6/2005 | Swayze et al. |
| 6,978,922 B2 | 12/2005 | Bilotti et al. |
| 7,000,818 B2 | 2/2006 | Shelton, IV et al. |
| 7,044,352 B2 | 5/2006 | Shelton, IV et al. |
| 7,114,642 B2 | 10/2006 | Whitman |
| 7,134,587 B2 | 11/2006 | Schwemberger et al. |
| 7,159,750 B2 | 1/2007 | Racenet et al. |
| 7,188,758 B2 | 3/2007 | Viola et al. |
| 7,210,609 B2 | 5/2007 | Leiboff et al. |
| 7,213,736 B2 | 5/2007 | Wales et al. |
| 7,278,563 B1 | 10/2007 | Green |
| RE40,237 E | 4/2008 | Bilotti et al. |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,208 B2 | 11/2008 | Wales et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,546,939 B2 | 6/2009 | Adams et al. |
| 7,546,940 B2 | 6/2009 | Milliman et al. |
| 7,549,564 B2 | 6/2009 | Boudreaux |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,644,848 B2 | 1/2010 | Swayze et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,695,485 B2 * | 4/2010 | Whitman ............ A61B 17/07207 606/142 |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,770,776 B2 | 8/2010 | Chen et al. |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,841,503 B2 | 11/2010 | Sonnenschein et al. |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,896,214 B2 | 3/2011 | Farascioni |
| 7,896,215 B2 | 3/2011 | Adams et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,934,630 B2 | 5/2011 | Shelton, IV et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,966,799 B2 | 6/2011 | Morgan et al. |
| 7,967,181 B2 | 6/2011 | Viola et al. |
| 7,980,443 B2 | 7/2011 | Scheib et al. |
| 7,988,028 B2 | 8/2011 | Farascioni et al. |
| 8,011,555 B2 | 9/2011 | Tarinelli et al. |
| 8,020,743 B2 | 9/2011 | Shelton, IV |
| 8,056,787 B2 | 11/2011 | Boudreaux et al. |
| 8,066,167 B2 | 11/2011 | Measamer et al. |
| 8,083,120 B2 | 12/2011 | Shelton, IV et al. |
| 8,113,410 B2 | 2/2012 | Hall et al. |
| 8,136,712 B2 | 3/2012 | Zingman |
| 8,136,713 B2 | 3/2012 | Hathaway et al. |
| 8,141,762 B2 | 3/2012 | Bedi et al. |
| 8,157,145 B2 | 4/2012 | Shelton, IV et al. |
| 8,157,153 B2 | 4/2012 | Shelton, IV et al. |
| 8,161,977 B2 | 4/2012 | Shelton, IV et al. |
| 8,167,185 B2 | 5/2012 | Shelton, IV et al. |
| 8,167,898 B1 * | 5/2012 | Schaller ............ A61B 17/07207 227/180.1 |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,215,531 B2 | 7/2012 | Shelton, IV et al. |
| 8,215,533 B2 | 7/2012 | Viola et al. |
| 8,220,688 B2 | 7/2012 | Laurent et al. |
| 8,220,690 B2 | 7/2012 | Hess et al. |
| 8,231,043 B2 | 7/2012 | Tarinelli et al. |
| 8,236,010 B2 | 8/2012 | Ortiz et al. |
| 8,241,322 B2 * | 8/2012 | Whitman ............ A61B 17/07207 227/175.1 |
| 8,267,300 B2 | 9/2012 | Boudreaux |
| 8,292,155 B2 | 10/2012 | Shelton, IV et al. |

(56) References Cited

U.S. PATENT DOCUMENTS

| | | |
|---|---|---|
| 8,308,046 B2 | 11/2012 | Prommersberger |
| 8,317,070 B2 | 11/2012 | Hueil et al. |
| 8,322,455 B2 | 12/2012 | Shelton, IV et al. |
| 8,322,589 B2 | 12/2012 | Boudreaux |
| 8,328,061 B2 * | 12/2012 | Kasvikis ............ A61B 17/07207 227/175.1 |
| 8,328,064 B2 | 12/2012 | Racenet et al. |
| 8,333,313 B2 | 12/2012 | Boudreaux et al. |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,365,975 B1 * | 2/2013 | Manoux ............ A61B 17/07207 227/176.1 |
| 8,365,976 B2 | 2/2013 | Hess et al. |
| 8,371,491 B2 | 2/2013 | Huitema et al. |
| 8,393,514 B2 | 3/2013 | Shelton, IV et al. |
| 8,397,971 B2 | 3/2013 | Yates et al. |
| 8,403,198 B2 | 3/2013 | Sorrentino et al. |
| 8,408,439 B2 | 4/2013 | Huang et al. |
| 8,408,442 B2 | 4/2013 | Racenet et al. |
| 8,413,871 B2 | 4/2013 | Racenet et al. |
| 8,414,577 B2 | 4/2013 | Boudreaux et al. |
| 8,424,740 B2 | 4/2013 | Shelton, IV et al. |
| 8,439,246 B1 | 5/2013 | Knodel et al. |
| 8,444,036 B2 | 5/2013 | Shelton, IV |
| 8,453,907 B2 | 6/2013 | Laurent et al. |
| 8,453,908 B2 | 6/2013 | Bedi et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,923 B2 | 6/2013 | Shelton, IV |
| 8,474,677 B2 | 7/2013 | Woodard, Jr. et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,517,239 B2 | 8/2013 | Scheib et al. |
| 8,517,243 B2 | 8/2013 | Giordano et al. |
| 8,517,244 B2 | 8/2013 | Shelton, IV et al. |
| 8,529,600 B2 | 9/2013 | Woodard, Jr. et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,561,870 B2 | 10/2013 | Baxter, III et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,584,919 B2 | 11/2013 | Hueil et al. |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,736 B2 | 1/2014 | Yates et al. |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,668,130 B2 | 3/2014 | Hess et al. |
| 8,672,207 B2 | 3/2014 | Shelton, IV et al. |
| 8,672,208 B2 | 3/2014 | Hess et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,708,213 B2 | 4/2014 | Shelton, IV et al. |
| 8,720,766 B2 | 5/2014 | Hess et al. |
| 8,727,197 B2 | 5/2014 | Hess et al. |
| 8,733,613 B2 | 5/2014 | Huitema et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,877 B2 | 7/2014 | Schall et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,814,024 B2 | 8/2014 | Woodard, Jr. et al. |
| 8,820,605 B2 | 9/2014 | Shelton, IV |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,465 B2 | 12/2014 | Shelton, Iv et al. |
| 8,899,466 B2 | 12/2014 | Baxter, III et al. |
| 8,911,471 B2 | 12/2014 | Spivey et al. |
| 8,925,782 B2 | 1/2015 | Shelton, IV |
| 8,925,788 B2 | 1/2015 | Hess et al. |
| 8,926,598 B2 | 1/2015 | Mollere et al. |
| 8,931,682 B2 | 1/2015 | Timm et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,016,542 B2 | 4/2015 | Shelton, IV et al. |
| 9,028,494 B2 | 5/2015 | Shelton, IV et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 * | 5/2015 | Schaller ............... A61B 17/064 |

(56) References Cited

U.S. PATENT DOCUMENTS

| | | | |
|---|---|---|---|
| 9,044,227 B2 | 6/2015 | Shelton, IV et al. | 227/176.1 |
| 9,044,228 B2 | 6/2015 | Woodard, Jr. et al. | |
| 9,044,230 B2 | 6/2015 | Morgan et al. | |
| 9,050,083 B2 | 6/2015 | Yates et al. | |
| 9,050,084 B2 | 6/2015 | Schmid et al. | |
| 9,055,941 B2 | 6/2015 | Schmid et al. | |
| 9,060,770 B2 | 6/2015 | Shelton, IV et al. | |
| 9,072,515 B2 | 7/2015 | Hall et al. | |
| 9,072,535 B2 | 7/2015 | Shelton, IV et al. | |
| 9,072,536 B2 | 7/2015 | Shelton, IV et al. | |
| 9,078,653 B2 | 7/2015 | Leimbach et al. | |
| 9,084,601 B2 | 7/2015 | Moore et al. | |
| 9,089,330 B2 | 7/2015 | Widenhouse et al. | |
| 9,095,339 B2 | 8/2015 | Moore et al. | |
| 9,101,358 B2 | 8/2015 | Kerr et al. | |
| 9,101,385 B2 | 8/2015 | Shelton, IV et al. | |
| 9,107,663 B2 | 8/2015 | Swensgard | |
| 9,113,862 B2 | 8/2015 | Morgan et al. | |
| 9,113,864 B2 | 8/2015 | Morgan et al. | |
| 9,113,865 B2 | 8/2015 | Shelton, IV et al. | |
| 9,113,874 B2 | 8/2015 | Shelton, IV et al. | |
| 9,113,883 B2 | 8/2015 | Aronhalt et al. | |
| 9,113,884 B2 | 8/2015 | Shelton, IV et al. | |
| 9,119,657 B2 | 9/2015 | Shelton, IV et al. | |
| 9,125,654 B2 | 9/2015 | Aronhalt et al. | |
| 9,125,662 B2 | 9/2015 | Shelton, IV | |
| 9,138,225 B2 | 9/2015 | Huang et al. | |
| 9,149,274 B2 | 10/2015 | Spivey et al. | |
| 2004/0094597 A1 | 5/2004 | Whitman et al. | |
| 2004/0199181 A1 | 10/2004 | Knodel et al. | |
| 2004/0222268 A1 | 11/2004 | Bilotti et al. | |
| 2005/0145675 A1 | 7/2005 | Hartwick et al. | |
| 2006/0011699 A1 | 1/2006 | Olson et al. | |
| 2006/0289602 A1 | 12/2006 | Wales et al. | |
| 2007/0027469 A1 | 2/2007 | Smith et al. | |
| 2007/0102472 A1 | 5/2007 | Shelton, IV | |
| 2007/0106317 A1 | 5/2007 | Shelton, IV et al. | |
| 2007/0170225 A1 | 7/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2007/0194079 A1 | 8/2007 | Hueil et al. | |
| 2007/0194082 A1 | 8/2007 | Morgan et al. | |
| 2007/0225562 A1 | 9/2007 | Spivey et al. | |
| 2007/0233163 A1 | 10/2007 | Bombard et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0078802 A1 | 4/2008 | Hess et al. | |
| 2008/0082125 A1 | 4/2008 | Murray et al. | |
| 2008/0169328 A1 | 7/2008 | Shelton | |
| 2008/0169332 A1 | 7/2008 | Shelton et al. | |
| 2008/0169333 A1 | 7/2008 | Shelton et al. | |
| 2008/0296346 A1 | 12/2008 | Shelton, IV et al. | |
| 2008/0308602 A1 | 12/2008 | Timm et al. | |
| 2008/0308603 A1 | 12/2008 | Shelton, IV et al. | |
| 2009/0001121 A1 | 1/2009 | Hess et al. | |
| 2009/0001130 A1 | 1/2009 | Hess et al. | |
| 2009/0005809 A1 | 1/2009 | Hess et al. | |
| 2009/0206125 A1 | 8/2009 | Huitema et al. | |
| 2009/0206126 A1 | 8/2009 | Huitema et al. | |
| 2009/0206131 A1 | 8/2009 | Weisenburgh, II et al. | |
| 2009/0206133 A1 | 8/2009 | Morgan et al. | |
| 2009/0206137 A1 | 8/2009 | Hall et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0242610 A1 | 10/2009 | Shelton, IV et al. | |
| 2009/0255978 A1 | 10/2009 | Viola et al. | |
| 2010/0012704 A1 | 1/2010 | Tarinelli Racenet et al. | |
| 2010/0069942 A1 | 3/2010 | Shelton, IV | |
| 2010/0133317 A1 | 6/2010 | Shelton, IV et al. | |
| 2010/0193566 A1 | 8/2010 | Scheib et al. | |
| 2010/0222901 A1 | 9/2010 | Swayze et al. | |
| 2010/0276471 A1 | 11/2010 | Whitman | |
| 2010/0305552 A1 | 12/2010 | Shelton, IV et al. | |
| 2011/0006101 A1 | 1/2011 | Hall et al. | |
| 2011/0024477 A1 | 2/2011 | Hall et al. | |
| 2011/0024478 A1 | 2/2011 | Shelton, IV | |
| 2011/0060363 A1 | 3/2011 | Hess et al. | |
| 2011/0087276 A1 | 4/2011 | Bedi et al. | |
| 2011/0095068 A1 | 4/2011 | Patel | |
| 2011/0114697 A1 | 5/2011 | Baxter, III et al. | |
| 2011/0125176 A1 | 5/2011 | Yates et al. | |
| 2011/0147433 A1 | 6/2011 | Shelton, IV et al. | |
| 2011/0155784 A1 | 6/2011 | Shelton, IV et al. | |
| 2011/0155786 A1 | 6/2011 | Shelton, IV | |
| 2011/0155787 A1 | 6/2011 | Baxter, III et al. | |
| 2011/0174861 A1 | 7/2011 | Shelton, IV et al. | |
| 2011/0174862 A1 | 7/2011 | Shelton, IV et al. | |
| 2011/0192882 A1 | 8/2011 | Hess et al. | |
| 2011/0275901 A1 | 11/2011 | Shelton, IV | |
| 2011/0276083 A1 | 11/2011 | Shelton, IV et al. | |
| 2011/0288573 A1 | 11/2011 | Yates et al. | |
| 2011/0290851 A1 | 12/2011 | Shelton, IV | |
| 2011/0290856 A1 | 12/2011 | Shelton, IV et al. | |
| 2011/0295269 A1 | 12/2011 | Swensgard et al. | |
| 2011/0295295 A1 | 12/2011 | Shelton, IV et al. | |
| 2012/0029272 A1 | 2/2012 | Shelton, IV et al. | |
| 2012/0071711 A1 | 3/2012 | Shelton, IV et al. | |
| 2012/0074200 A1 | 3/2012 | Schmid et al. | |
| 2012/0080336 A1 | 4/2012 | Shelton, IV et al. | |
| 2012/0080338 A1 | 4/2012 | Shelton, IV et al. | |
| 2012/0080340 A1 | 4/2012 | Shelton, IV et al. | |
| 2012/0080344 A1 | 4/2012 | Shelton, IV | |
| 2012/0080478 A1 | 4/2012 | Morgan et al. | |
| 2012/0080488 A1 | 4/2012 | Shelton, IV et al. | |
| 2012/0080498 A1 | 4/2012 | Shelton, IV et al. | |
| 2012/0083835 A1 | 4/2012 | Shelton, IV et al. | |
| 2012/0199632 A1 | 8/2012 | Spivey et al. | |
| 2012/0223123 A1 | 9/2012 | Baxter, III et al. | |
| 2012/0234895 A1 | 9/2012 | O'Connor et al. | |
| 2012/0234897 A1 | 9/2012 | Shelton, IV et al. | |
| 2012/0234899 A1 | 9/2012 | Scheib et al. | |
| 2012/0238823 A1 | 9/2012 | Hagerty et al. | |
| 2012/0241491 A1 | 9/2012 | Aldridge et al. | |
| 2012/0241492 A1 | 9/2012 | Shelton, IV et al. | |
| 2012/0241493 A1 | 9/2012 | Baxter, III et al. | |
| 2012/0241496 A1 | 9/2012 | Mandakolathur Vasudevan et al. | |
| 2012/0241497 A1 | 9/2012 | Mandakolathur Vasudevan et al. | |
| 2012/0241498 A1 | 9/2012 | Gonzalez et al. | |
| 2012/0241499 A1 | 9/2012 | Baxter, III et al. | |
| 2012/0241500 A1 | 9/2012 | Timmer et al. | |
| 2012/0241501 A1 | 9/2012 | Swayze et al. | |
| 2012/0241502 A1 | 9/2012 | Aldridge et al. | |
| 2012/0241503 A1 | 9/2012 | Baxter, III et al. | |
| 2012/0241505 A1 | 9/2012 | Alexander, III et al. | |
| 2012/0248169 A1 | 10/2012 | Widenhouse et al. | |
| 2012/0253298 A1 | 10/2012 | Henderson et al. | |
| 2012/0283707 A1 | 11/2012 | Giordano et al. | |
| 2012/0283748 A1 | 11/2012 | Ortiz et al. | |
| 2012/0292367 A1 | 11/2012 | Morgan et al. | |
| 2012/0298722 A1 | 11/2012 | Hess et al. | |
| 2012/0312860 A1 | 12/2012 | Ming et al. | |
| 2012/0318842 A1 | 12/2012 | Anim et al. | |
| 2012/0318843 A1 | 12/2012 | Henderson et al. | |
| 2012/0318844 A1 | 12/2012 | Shelton, IV et al. | |
| 2013/0020375 A1 | 1/2013 | Shelton, IV et al. | |
| 2013/0020376 A1 | 1/2013 | Shelton, IV et al. | |
| 2013/0023861 A1 | 1/2013 | Shelton, IV et al. | |
| 2013/0026208 A1 | 1/2013 | Shelton, IV et al. | |
| 2013/0026210 A1 | 1/2013 | Shelton, IV et al. | |
| 2013/0056518 A1 | 3/2013 | Swensgard | |
| 2013/0075449 A1 | 3/2013 | Schmid et al. | |
| 2013/0079814 A1 | 3/2013 | Hess et al. | |
| 2013/0087597 A1 | 4/2013 | Shelton, IV et al. | |
| 2013/0098970 A1 | 4/2013 | Racenet et al. | |
| 2013/0116668 A1 | 5/2013 | Shelton, IV et al. | |
| 2013/0116669 A1 | 5/2013 | Shelton, IV et al. | |
| 2013/0126582 A1 | 5/2013 | Shelton, IV et al. | |
| 2013/0146641 A1 | 6/2013 | Shelton, IV et al. | |
| 2013/0146642 A1 | 6/2013 | Shelton, IV et al. | |

(56) References Cited

U.S. PATENT DOCUMENTS

| | | |
|---|---|---|
| 2013/0146643 A1 | 6/2013 | Schmid et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0161375 A1 | 6/2013 | Huitema et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0248576 A1 | 9/2013 | Laurent et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005679 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005708 A1 | 1/2014 | Shelton, IV |
| 2014/0005718 A1 | 1/2014 | Shelton, IV et al. |
| 2014/0008414 A1 | 1/2014 | Shelton, IV et al. |
| 2014/0014705 A1 | 1/2014 | Baxter, III |
| 2014/0042205 A1 | 2/2014 | Baxter, III et al. |
| 2014/0048582 A1 | 2/2014 | Shelton, IV et al. |
| 2014/0061279 A1 | 3/2014 | Laurent et al. |
| 2014/0097227 A1 | 4/2014 | Aronhalt et al. |
| 2014/0107640 A1 | 4/2014 | Yates et al. |
| 2014/0128850 A1 | 5/2014 | Kerr et al. |
| 2014/0151433 A1 | 6/2014 | Shelton, IV et al. |
| 2014/0151434 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0236184 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263564 A1 | 9/2014 | Leimbach et al. |
| 2014/0263565 A1 | 9/2014 | Lytle, IV et al. |
| 2014/0263571 A1 | 9/2014 | Morgan et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305993 A1 | 10/2014 | Timm et al. |
| 2014/0305994 A1 | 10/2014 | Parihar et al. |
| 2014/0305995 A1 | 10/2014 | Shelton, IV et al. |
| 2014/0309665 A1 | 10/2014 | Parihar et al. |

(56) References Cited

U.S. PATENT DOCUMENTS

| | | |
|---|---|---|
| 2014/0309666 A1 | 10/2014 | Shelton, IV et al. |
| 2014/0326777 A1 | 11/2014 | Zingman |
| 2014/0330161 A1 | 11/2014 | Swayze et al. |
| 2014/0352463 A1 | 12/2014 | Parihar |
| 2014/0353358 A1 | 12/2014 | Shelton, IV et al. |
| 2014/0353359 A1 | 12/2014 | Hall et al. |
| 2014/0367447 A1 | 12/2014 | Woodard, Jr. et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0090765 A1 | 4/2015 | Hess et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0144678 A1 | 5/2015 | Hall et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289870 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |

(56) References Cited

FOREIGN PATENT DOCUMENTS

| | | |
|---|---|---|
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101541251 A | 9/2009 |
| CN | 101675898 A | 3/2010 |
| CN | 101683280 A | 3/2010 |
| CN | 102188270 A | 9/2011 |
| CN | 101534723 B | 1/2012 |
| CN | 101507633 B | 2/2013 |
| CN | 101023879 B | 3/2013 |
| CN | 101401736 B | 6/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 A1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 81 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |

(56) References Cited

FOREIGN PATENT DOCUMENTS

| | | |
|---|---|---|
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1806103 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 2110083 A2 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000102 A2 | 12/2008 |
| EP | 2005894 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |

(56) References Cited

FOREIGN PATENT DOCUMENTS

| | | |
|---|---|---|
| EP | 2077093 A2 | 7/2009 |
| EP | 1745748 B1 | 8/2009 |
| EP | 2090231 A1 | 8/2009 |
| EP | 2090237 A1 | 8/2009 |
| EP | 2090241 A1 | 8/2009 |
| EP | 2090244 A2 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110084 A2 | 10/2009 |
| EP | 2111803 A2 | 10/2009 |
| EP | 1762190 B8 | 11/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 1566150 B1 | 4/2010 |
| EP | 1813206 B1 | 4/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2286738 A2 | 2/2011 |
| EP | 1690502 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2399538 A2 | 12/2011 |
| EP | 1785102 B1 | 1/2012 |
| EP | 2090253 B1 | 3/2012 |
| EP | 2430986 A2 | 3/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2005895 B1 | 8/2012 |
| EP | 2090248 B1 | 8/2012 |
| EP | 2481359 A1 | 8/2012 |
| EP | 1935351 B1 | 9/2012 |
| EP | 2497431 A1 | 9/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| EP | 2090238 B1 | 4/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 1772105 B1 | 5/2014 |
| EP | 2446835 B1 | 1/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 93100110 A | 11/1993 |
| JP | 50-33988 U | 4/1975 |
| JP | S 58500053 A | 1/1983 |
| JP | S 59-174920 A | 3/1984 |
| JP | 60-100955 A | 6/1985 |
| JP | 60-212152 A | 10/1985 |
| JP | 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | 63-203149 | 8/1988 |
| JP | H 02-279149 A | 11/1990 |
| JP | 3-12126 A | 1/1991 |
| JP | H 04-215747 A | 8/1992 |
| JP | H 4-131860 U | 12/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |

(56) References Cited

FOREIGN PATENT DOCUMENTS

| | | |
|---|---|---|
| JP | H 06-327684 A | 11/1994 |
| JP | 7-31623 A | 2/1995 |
| JP | 7051273 A | 2/1995 |
| JP | H 7-47070 A | 2/1995 |
| JP | 7-124166 A | 5/1995 |
| JP | H 7-163574 A | 6/1995 |
| JP | 07-171163 | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 8-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-14632 | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 | 6/2003 |
| JP | 2003-521301 A | 7/2003 |
| JP | 2003-523251 A | 8/2003 |
| JP | 2003-523254 A | 8/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-334412 A | 12/2006 |
| JP | 2006-334417 A | 12/2006 |
| JP | 2006-346445 A | 12/2006 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 4001860 B2 | 10/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-259860 A | 10/2008 |
| JP | 2008-264535 A | 11/2008 |
| JP | 2008-283459 A | 11/2008 |
| JP | 2009-502351 A | 1/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-536082 A | 10/2009 |
| JP | 2009-261944 A | 11/2009 |
| JP | 2009-539420 A | 11/2009 |
| JP | 2010-504808 A | 2/2010 |
| JP | 2010-504809 A | 2/2010 |
| JP | 2010-505524 A | 2/2010 |
| JP | 2010-069310 A | 4/2010 |
| JP | 2010-088876 A | 4/2010 |
| JP | 2010-098844 A | 4/2010 |
| JP | 4549018 B2 | 9/2010 |
| JP | 2010-540192 A | 12/2010 |
| JP | 4783373 B2 | 7/2011 |
| JP | 5140421 B2 | 2/2013 |
| JP | 5162595 B2 | 3/2013 |
| JP | 2013-128791 A | 7/2013 |
| JP | 5333899 B2 | 11/2013 |

(56) References Cited

FOREIGN PATENT DOCUMENTS

| | | |
|---|---|---|
| KR | 20110003229 A | 1/2011 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A1 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |

(56) References Cited

FOREIGN PATENT DOCUMENTS

| | | |
|---|---|---|
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 5/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A1 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A2 | 3/2010 |
| WO | WO 2010/050771 A2 | 5/2010 |
| WO | WO 2010/054404 A1 | 5/2010 |
| WO | WO 2010/063795 A1 | 6/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/044343 A2 | 4/2011 |

(56) References Cited

FOREIGN PATENT DOCUMENTS

| WO | WO 2011/060311 A2 | 5/2011 |
|---|---|---|
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/143913 A2 | 10/2012 |
| WO | WO 2012/148667 A2 | 11/2012 |
| WO | WO 2012/148703 A2 | 11/2012 |
| WO | WO 2013/043707 A2 | 3/2013 |
| WO | WO 2013/043717 A1 | 3/2013 |
| WO | WO 2013/043721 A2 | 3/2013 |
| WO | WO 2013/148762 A2 | 10/2013 |
| WO | WO 2013/167427 A1 | 11/2013 |

OTHER PUBLICATIONS

Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print. cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels", Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluroran to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.

\* cited by examiner

US 9,386,985 B2

SURGICAL CUTTING INSTRUMENT

BACKGROUND

The present disclosure relates, in general, to surgery, and in particular, to a surgical transaction or cutting tool which may be used to cut tissue alone or as a part of surgical tissue cutting and fastening instrument.

During many surgical procedures, it is common to use a tissue fastening and cutting device, such as a linear cutter, for fastening and transecting tissue in order to resect the tissue and achieve hemostasis by placing a plurality of laterally spaced rows of staples on opposite sides of a tissue cut or tissue transection line. Surgical fastening and cutting instruments are generally used to make a longitudinal incision in tissue and apply lines of staples on opposing sides of the incision. Such instruments commonly include an end effector having a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil. A cutting instrument is drawn distally along the jaw member so that the clamped tissue is cut and fastened (e.g., stapled).

An example of a surgical fastening and cutting instrument suitable for endoscopic applications is described in U.S. Pat. No. 7,000,818, entitled SURGICAL STAPLING INSTRUMENT HAVING SEPARATE DISTINCT CLOSING AND FIRING SYSTEMS, which issued on Feb. 21, 2006, the entire disclosure of which is hereby incorporated by reference herein. In use, a clinician is able to close the jaw members of the instrument upon tissue to position the tissue prior to firing. Once the clinician has determined that the jaw members are properly gripping tissue, the clinician can then fire the surgical instrument, thereby severing and stapling the tissue. An example of a Motor-driven surgical fastening and cutting instrument is described in U.S. Pat. No. 7,416,101, entitled "MOTOR-DRIVEN SURGICAL CUTTING AND FASTENING INSTRUMENT WITH LOADING FORCE FEEDBACK, which issued on Aug. 26, 2008, the entire disclosure of which is hereby incorporated by reference herein.

BRIEF DESCRIPTION OF THE DRAWINGS

The novel features of the various embodiments of the invention are set forth with particularity in the appended claims. The various embodiments of the invention, however, both as to organization and methods of operation, together with further objects and advantages thereof, may best be understood by reference to the following description, taken in conjunction with the accompanying drawings as follows.

SUMMARY

Figure 1:
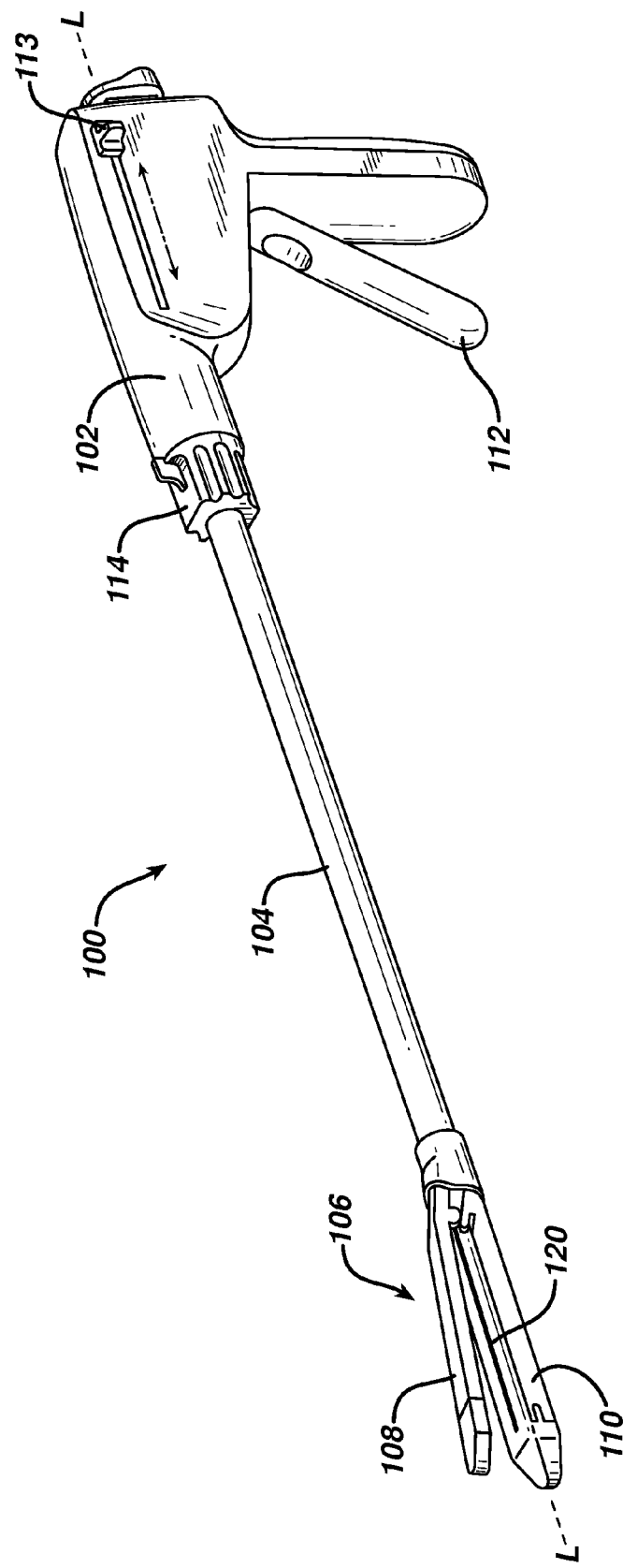
FIG. 1 is a prospective view of a surgical cutting instrument including a handle, a shaft and an end effector.

A surgical cutting instrument may comprise a first jaw member, a second jaw member movably supported relative to the first jaw member for selective movement between an open position and a closed position to clamp tissue therebetween upon application of a closing motion thereto, and a cutting member comprising a tissue cutting edge to cut the tissue clamped between the first jaw member and the second jaw member upon application of a retraction motion to the cutting member.

A surgical staple cartridge assembly for use with a surgical stapler may include a staple cartridge housing configured to be operably supported in the surgical stapler, wherein the staple cartridge housing may include a top surface, a slot, and at least one staple cavity. The surgical cartridge assembly may further include a cutting member positioned within the staple cartridge housing, the cutting member comprising a tissue cutting edge configured to cut tissue, wherein the cutting member is proximally retractable upon application of a retraction motion thereto, and wherein the tissue cutting edge is proximally presented as the cutting member is proximally retracted through the tissue.

A surgical cutting and fastening instrument may include an elongate shaft, an elongate channel operably coupled to the elongate shaft and configured to operably support a staple cartridge therein, and an anvil movably supported relative to the elongate channel for selective movement between an open position and a closed position, wherein tissue is clamped between the anvil and a staple cartridge supported within the elongate channel in response to opening and closing motions applied thereto from the elongate shaft. The surgical instrument may further include a cutting member comprising a tissue cutting edge, wherein the cutting member is retractable relative to the elongate channel, and wherein the tissue cutting edge is configured to cut tissue clamped between the anvil and the staple cartridge during retraction of the cutting member.

A surgical cutting and fastening instrument comprises a first jaw having a housing, the housing including a top surface, a second jaw movably supported relative to the first jaw upon application of opening and closing motions thereto, and a cutting member including a tissue cutting edge, the cutting member being movable from a proximal starting position to a distal ending position upon application of a firing motion thereto, and from the distal ending position to the proximal starting position upon application of a retraction motion thereto, the cutting member being further movably supported within the housing of the first jaw such that when the cutting member is moving from the proximal starting position to the distal ending position, the tissue cutting edge is positioned below the top surface of the housing of the first jaw, and when the cutting member is moving from the distal ending position to the proximal starting position, the tissue cutting edge extends above the top surface of the housing of the first jaw.

A surgical staple cartridge comprises a cartridge housing including a top surface, the cartridge housing operably supporting a plurality of surgical staples therein, and a cutting member movably supported within the cartridge housing and including a tissue cutting edge, the cutting member being movable from a proximal starting position to a distal ending position, and from the distal ending position to the proximal starting position, the cutting member further being movably supported within the cartridge housing such that when the cutting member is moving from the proximal starting position to the distal ending position, the tissue cutting edge is positioned below the top surface, and when the cutting member is moving from the distal ending position to the proximal starting position, the tissue cutting edge extends above the top surface.

DESCRIPTION

As generally used herein, the terms "proximal" and "distal" generally refer to a clinician manipulating one end of an instrument used to treat a patient. The term "proximal" generally refers to the portion of the instrument closest to the clinician. The term "distal" generally refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Referring to FIG. 1, a surgical instrument, generally 100, can comprise a handle 102, a shaft 104, and an end effector 106. In at least one embodiment, as shown in FIG. 1, the end effector 106 may comprise a first jaw member 108 and a second jaw member 110. The end effector 106 may be configured to perform surgical activities in response to drive motions applied thereto. The first jaw member 108 may be movable relative to the second jaw member 110 between a first position and a second position. The first position may be an open position and the second position may be a closed position. In at least one embodiment, referring to FIG. 1, the first jaw member 108 may be pivotally coupled to the second jaw member 110. Other suitable arrangements for coupling the first jaw member 108 and the second jaw member 110 are contemplated within the scope of this disclosure.

Referring again to FIG. 1, the handle 102 may comprise a closure actuator 112, a firing actuator 113, and a rotation actuator 114. The closure actuator 112 may be pivotally coupled to handle 102. Actuation of the closure actuator 112 may cause the first jaw member 108 to move relative to the second jaw member 110. Rotating the rotation actuator 114 may result in rotation of the end effector 106 about a longitudinal axis L-L.

Figure 2:
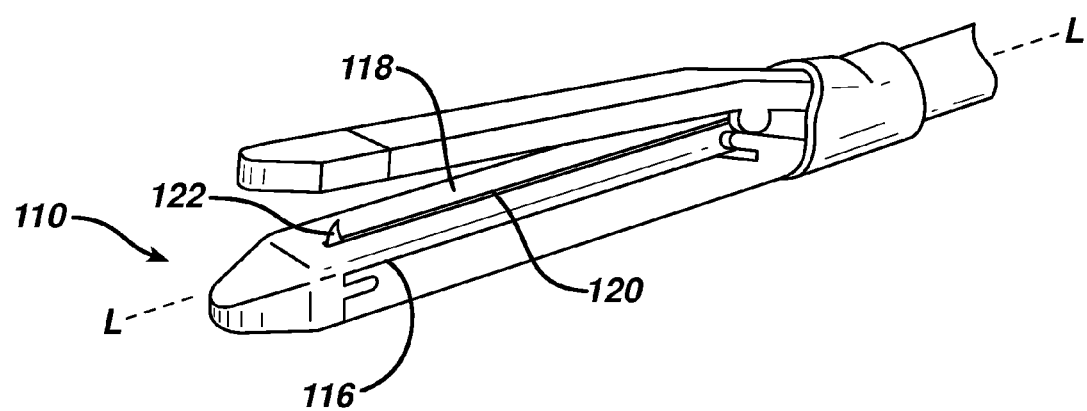
FIG. 2 is a prospective view of a lower jaw of the end effector of the surgical cutting instrument of FIG. 1.

Referring to FIGS. 2-7, the second jaw member 110 may comprise a housing 116 including a top surface 118 having a slot 120 extending along the longitudinal axis L-L. As illustrated in FIG. 2, the housing 116 may include a cutting member 122 which may travel through slot 120 along the longitudinal axis L-L. As illustrated in the exploded view in FIG. 3, the housing 116 may include a first track 124, and a second track 126. Tracks 124 and 126 may extend along the longitudinal axis L-L such that they are parallel with each other. In addition, tracks 124 and 126 may extend in a plane that is substantially perpendicular to the top surface 118, where, in at least one embodiment, the second track 126 is closer to the top surface 118 than the first track 124. A distal portion 128 of the first track 124 may converge to intersect with the second track 126 at a junction point 130. Tracks 124 and 126 may further extend distally beyond junction point 130 forming a common track portion 132.

Referring again to FIGS. 2-7, the cutting member 122 may include a tissue cutting edge 134, a first pin 136, a second pin 138, and an engagement portion 140. The cutting member 122 may travel between a proximal starting position 142 as illustrated in FIG. 4, and a distal ending position 144 as illustrated in FIG. 6. At the proximal starting position 142, the first pin 136 may ride in the first track 124, and the second pin 138 may ride in the second track 126, causing the cutting member 122 to remain in an "undeployed" orientation. In the undeployed orientation, as illustrated in FIG. 4, the tissue cutting edge 134 is not exposed above the top surface 118.

Figure 3:
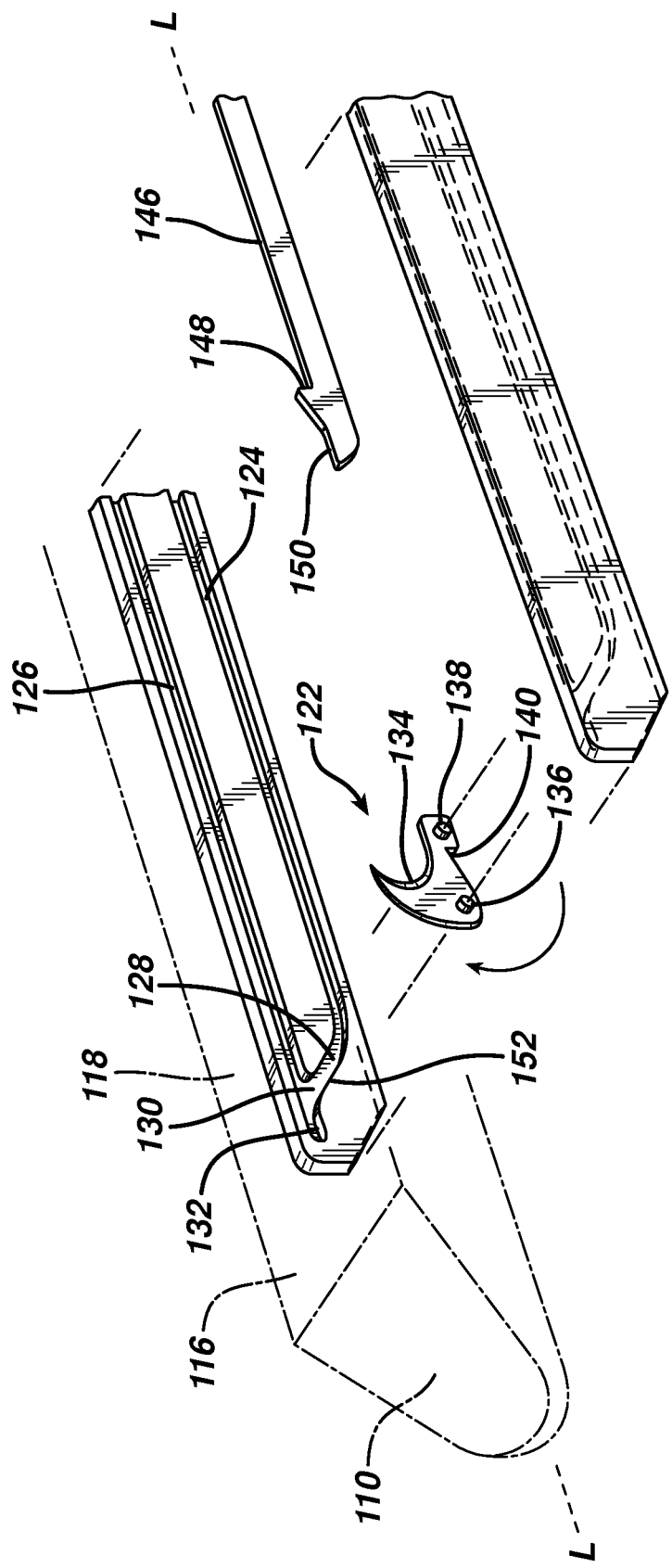
FIG. 3 is a partial exploded view of the lower jaw of the end effector of the surgical cutting instrument of FIG. 1.
Figure 4:
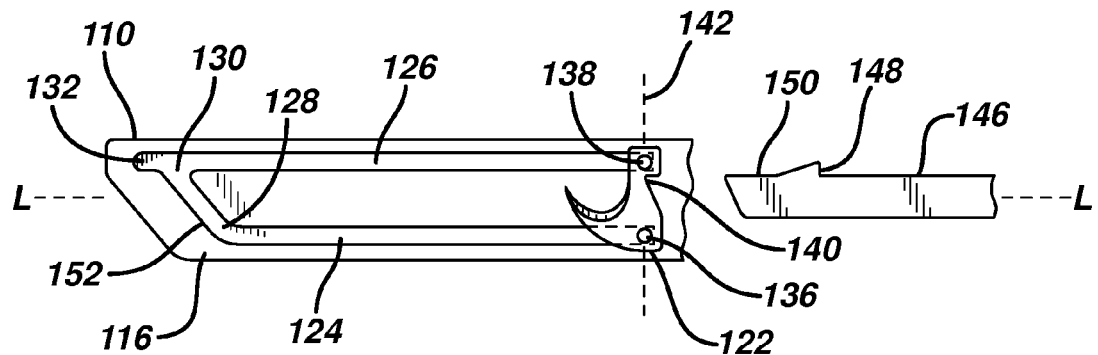
FIG. 4 is a partial cross-sectional view of the lower jaw of the end effector of the surgical cutting instrument of FIG. 1.

As illustrated in the exploded view in FIG. 3, the surgical instrument 100 may further comprise a driving member 146, which may include a retraction hook 148 and a driving tip 150. The driving member 146 may be operably coupled, at a proximal portion thereof, to the firing actuator 113 such that an operator of the surgical instrument 100 may advance the driving member 146 distally by advancing the firing actuator 113 distally, and may retract the driving member 146 proximally by retracting firing actuator 113 proximally.

Figure 5:
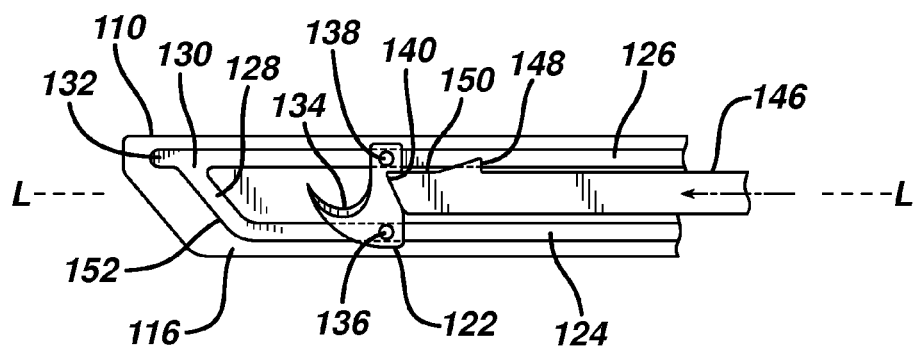
FIG. 5 is a partial cross-sectional view of the lower jaw of the end effector of the surgical cutting instrument of FIG. 1.
Figure 6:
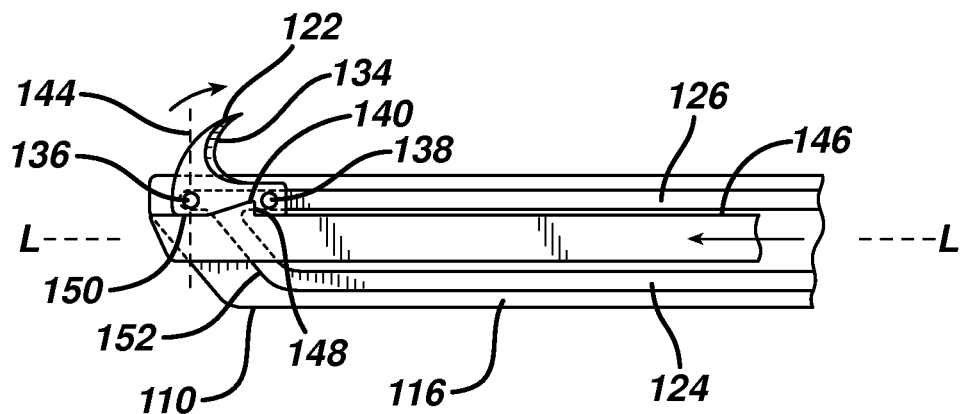
FIG. 6 is a partial cross-sectional view of the lower jaw of the end effector of the surgical cutting instrument of FIG. 1.

Referring to FIGS. 4 and 5, advancing the driving member 146 distally may bring the driving tip 150 into mating engagement with engagement portion 140 of cutting member 122. With the first pin 136 riding in the first track 124, and the second pin 138 riding in the second track 126, further advancing of the driving member 146 may enable the cutting member 122 to travel distally from the proximal starting position 142 through slot 120 as illustrated in FIG. 5.

Referring to FIGS. 5 and 6, the cutting member 122 may be advanced distally in an undeployed orientation along tracks 124 and 126 until the first pin 136 enters the distal portion 128 of the first track 124. The distal portion 128 may comprise a camming surface 152 which may cause the first pin 136 to be lifted toward junction point 130 as the cutting member 122 continues to be advanced distally. In result, the cutting member 122 is transitioned gradually from an undeployed orientation, as illustrated in FIG. 5, wherein the tissue cutting edge 134 is not exposed above top surface 118, to a deployed orientation, as illustrated in FIG. 6, wherein the tissue cutting edge 134 is exposed above top surface 118. Said another way, advancing the first pin 136 against the camming surface 152 may cause the cutting member 122 to move about an axis transverse to the longitudinal axis L-L resulting in deployment of the tissue cutting edge 134.

Referring again to FIGS. 5 and 6, as the cutting member 122 transitions from an undeployed orientation to a deployed orientation, as described above, the first pin 136 may enter the common track portion 132. In addition, the engagement portion 140 of the cutting member 122 may be released from mating engagement with the driving tip 150 and may enter into a mating engagement with the retraction hook 148 as illustrated in FIG. 6.

Figure 7:
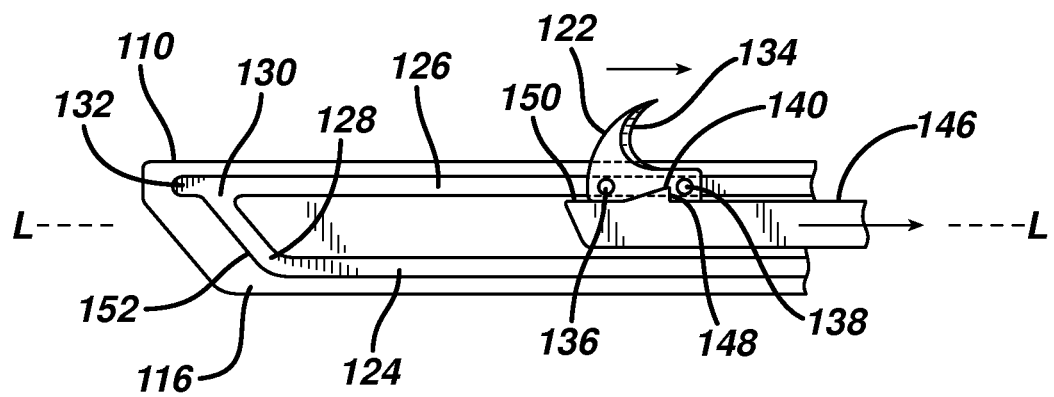
FIG. 7 is a partial cross-sectional view of the lower jaw of the end effector of the surgical cutting instrument of FIG. 1.
Figure 8:
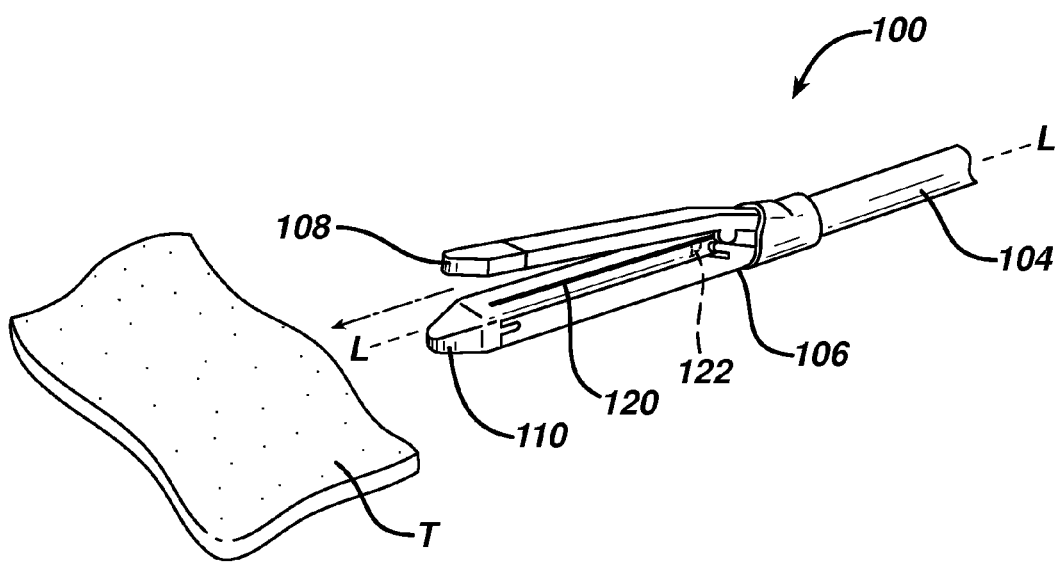
FIG. 8 is a prospective view of the end effector of the surgical cutting instrument of FIG. 1 near tissue.

Referring now to FIGS. 6 and 7, the deployed cutting member 122 may then travel proximally from the distal ending position 144 toward the proximal starting position 142 in response to retraction motions by the driving member 146. As illustrated in FIG. 6, the tissue cutting edge 134 is proximally presented at the distal ending position 144. Retraction of the driving member 146 may cause the cutting member 122 to travel proximally along the longitudinal axis L-L. As the cutting member 122 begins to travel proximally, the first pin 136 rides in common track portion 132, and the second pin 138 rides in the second track 126. Upon reaching junction point 130, the first pin 136 is prevented from reentering the distal portion 128 of the first track 124 by driving member 146. Instead, the first pin 136 enters the second track 126. As illustrated in FIG. 7, both pins 136 and 138 may ride in the second track 126 for a remainder of the proximal travel of the cutting member 122.

In certain embodiments, the first jaw member 108 may comprise a slot (not shown) corresponding to slot 120 in the second jaw member 110. The slot of the first jaw member 108 may also extend along the longitudinal axis L-L, and may receive a top portion of the section of the deployed cutting member 122 exposed above top surface 118 during retraction of the cutting member 122 through slot 120.

Figure 9:
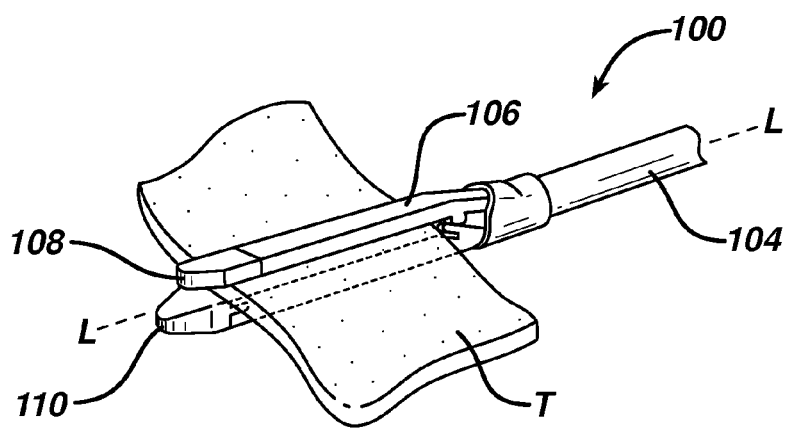
FIG. 9 is a prospective view of the end effector of the surgical cutting instrument of FIG. 1 clamping tissue.
Figure 10:
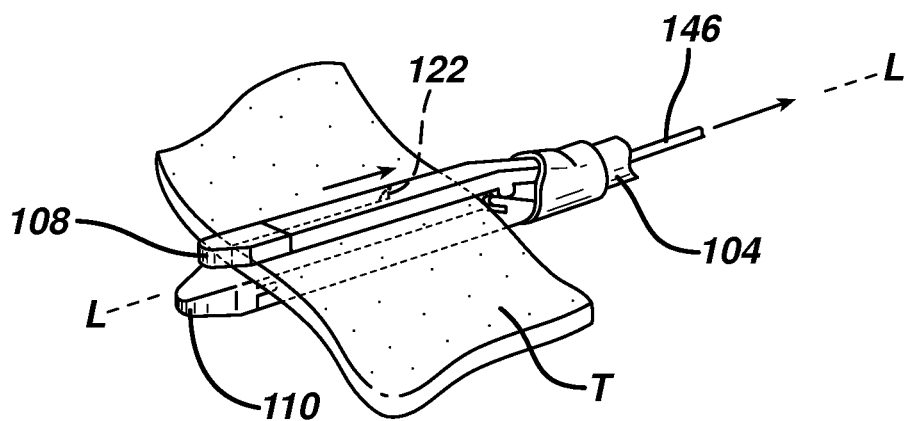
FIG. 10 is a prospective view of the end effector of the surgical cutting instrument of FIG. 1 clamping tissue, and a cutting member cutting through the tissue.
Figure 11:
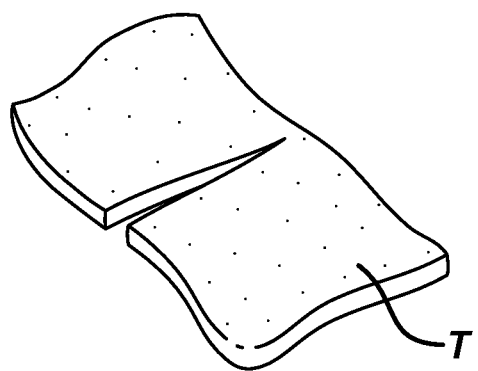
FIG. 11 is a prospective view of tissue cut by the surgical cutting instrument of FIG. 1.

Referring now to FIGS. 8-11, the surgical instrument 100 can be used in performing a surgical tissue transection procedure. An operator may actuate the closure actuator 112 of the handle 102 to grasp and secure tissue between the first jaw member 108 and the second jaw member 110 as illustrated in FIG. 9. The operator may then deploy the cutting member 122 by advancing the firing actuator 113 as described above. Upon deployment, the cutting member 122 can be retracted by retracting the firing actuator 113. The proximally presented tissue cutting edge 134 may cut through the tissue grasped between jaw members 108 and 110 as the cutting member 122 is retracted proximally. Transected tissue may then be released from end effector 106 by actuating the closure actuator 112 to open the jaw members 108 and 110.

Figure 12:
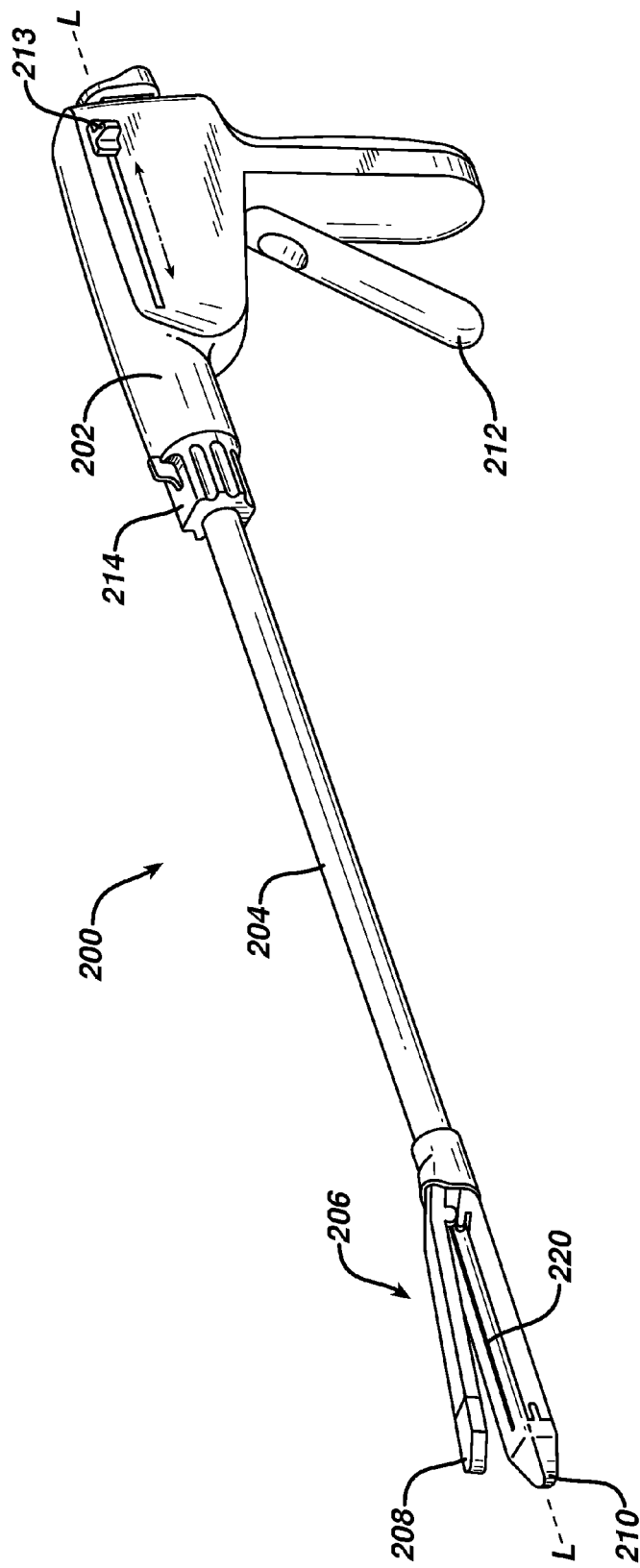
FIG. 12 is a prospective view of a surgical cutting instrument including a handle, a shaft and an end effector.

Referring to FIG. 12, a surgical instrument, generally 200, can comprise a handle 202, a shaft 204, and an end effector 206. In at least one embodiment, as shown in FIG. 12, the end effector 206 may comprise a first jaw member 208 and a second jaw member 210. The end effector 206 may be configured to perform surgical activities in response to drive motions applied thereto. The first jaw member 208 may be movable relative to the second jaw member 210 between a first position and a second position. The first position may be an open position and the second position may be a closed position. In at least one embodiment, referring to FIG. 12, the first jaw member 208 may be pivotally coupled to the second jaw member 210. Other suitable arrangements for coupling the first jaw member 208 and the second jaw member 210 are contemplated within the scope of this disclosure.

Referring again to FIG. 12, the handle 202 may comprise a closure actuator 212, a firing actuator 213, and a rotation actuator 214. The closure actuator 212 may be pivotally coupled to handle 202. Actuation of the closure actuator 212 may cause the first jaw member 208 to move relative to the second jaw member 210. Rotating the rotation actuator 214 may result in rotation of the end effector 206 about a longitudinal axis L-L.

Figure 13:
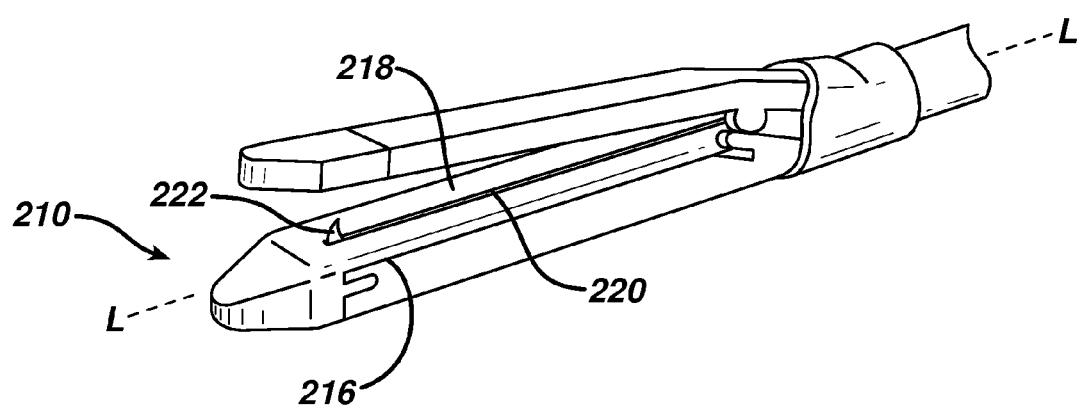
FIG. 13 is a prospective view of a lower jaw of the end effector of the surgical cutting instrument of FIG. 12.
Figure 14:
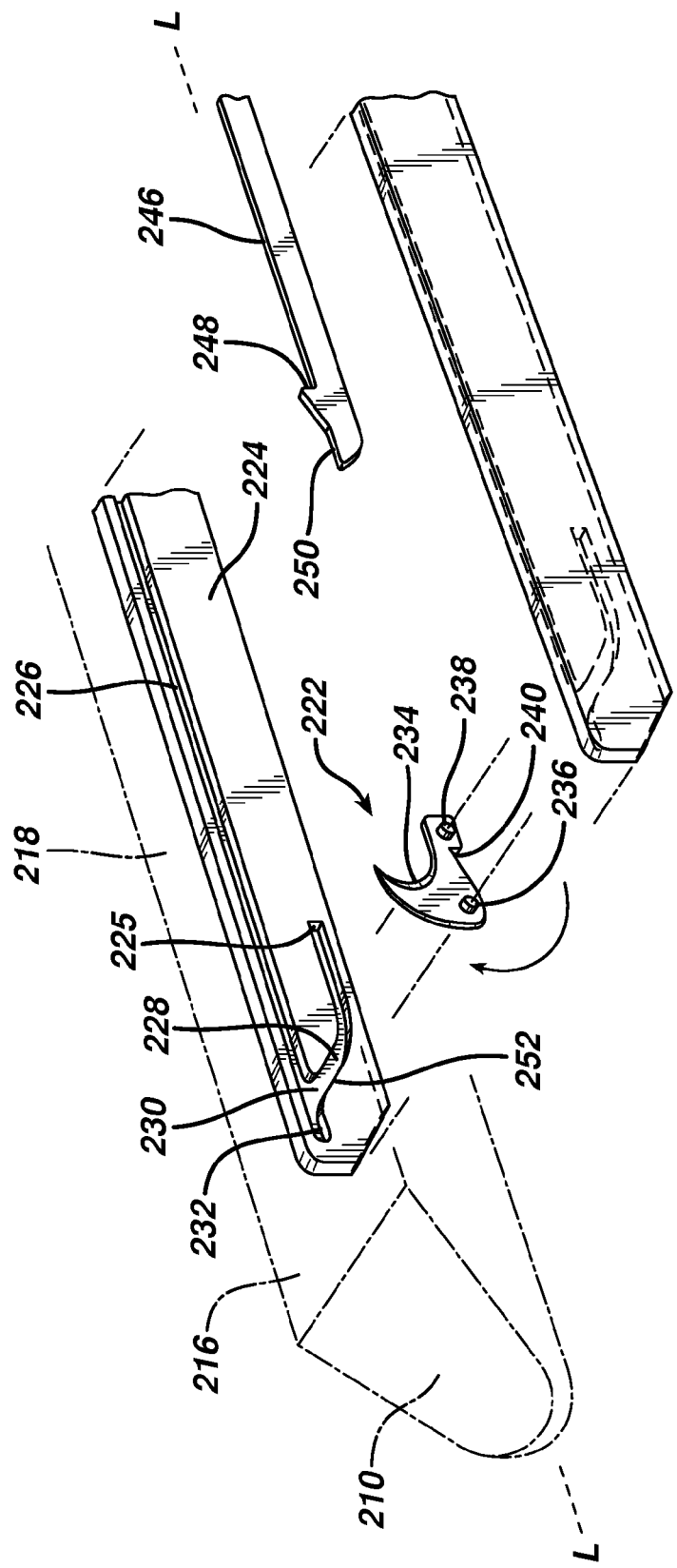
FIG. 14 is a partial exploded view of the lower jaw of the end effector of the surgical cutting instrument of FIG. 12.
Figure 15:
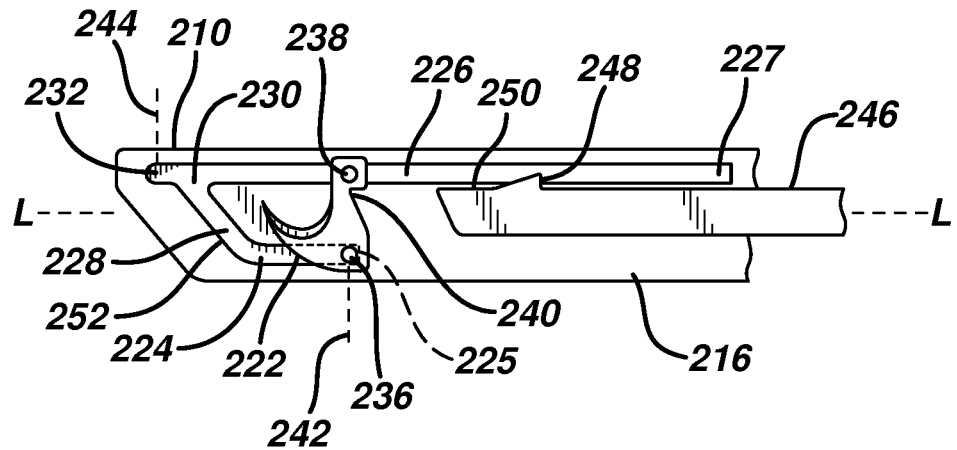
FIG. 15 is a partial cross-sectional view of the lower jaw of the end effector of the surgical cutting instrument of FIG. 12.

Referring to FIGS. 13-18, the second jaw member 210 may comprise a housing 216 including a top surface 218 having a slot 220 extending along the longitudinal axis L-L. As illustrated in FIG. 13, the housing 216 may include a cutting member 222 which may travel through slot 220 along the longitudinal axis L-L. As illustrated in the exploded view in FIG. 14, the housing 216 may include a first track 224, and a second track 226. Tracks 224 and 226 may extend along the longitudinal axis L-L such that they are substantially parallel with each other. In addition, tracks 224 and 226 may extend in a plane that is substantially perpendicular to the top surface 218, wherein the second track 226 is closer to the top surface 218 than the first track 224. As illustrated in FIG. 15, the first track 224 may begin at a starting point 225 positioned at a distal portion of the housing 216; and the second track 226 may begin a starting point 227 positioned at a proximal portion of the housing 216. Such arrangement shortens the distance that the cutting member 222 must travel distally before being moved to the deployed orientation.

Referring again to FIGS. 13-18, a distal portion 228 of the first track 224 may converge to intersect with the second track 226 at a junction point 230. Tracks 224 and 226 may further extend distally beyond junction point 230 forming a common track portion 232. The cutting member 222 may include a tissue cutting edge 234, a first pin 236, a second pin 238, and an engagement portion 240. The cutting member 222 may travel between a proximal starting position 242, which may be defined by the starting point 225 of the first track 224 as illustrated in FIG. 15, and a distal ending position 244 at a distal end of the common track 232 as illustrated in FIG. 17. At the proximal starting position 242, the first pin 236 may ride in the first track 224, and the second pin 238 may ride in the second track 226, causing the cutting member 222 to remain in an undeployed orientation. In the undeployed orientation, as illustrated in FIG. 15, the tissue cutting edge 234 of the cutting member 222 is not exposed above the top surface 218.

As illustrated in the exploded view in FIG. 14, the surgical instrument 200 may further comprise a driving member 246, which may include a retraction hook 248 and a driving tip 250. The driving member 246 may be operably coupled, at a proximal portion thereof, to the firing actuator 213 such that an operator of the surgical instrument 200 may advance the driving member 246 distally by advancing the firing actuator 213 distally, and may retract the driving member 246 proximally by retracting firing actuator 213 proximally.

Figure 16:
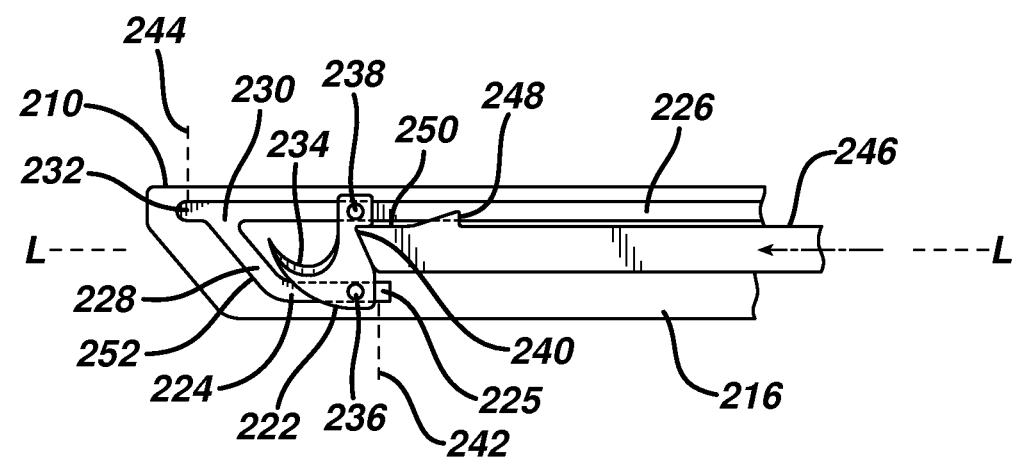
FIG. 16 is a partial cross-sectional view of the lower jaw of the end effector of the surgical cutting instrument of FIG. 12.
Figure 17:
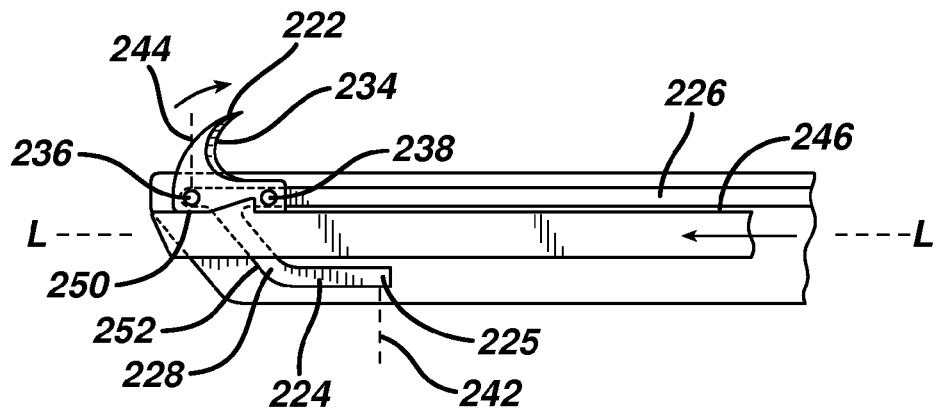
FIG. 17 is a partial cross-sectional view of the lower jaw of the end effector of the surgical cutting instrument of FIG. 12.

Referring to FIGS. 15 and 16, advancing the driving member 246 distally may bring the driving tip 250 into mating engagement with engagement portion 240 of cutting member 222. With the first pin 236 riding in the first track 224, and the second pin 238 riding in the second track 226, further advancing of the driving member 246 may enable the cutting member 222 to travel a short distance distally from the proximal starting position 242 through slot 218 as illustrated in FIG. 16.

Referring to FIGS. 16 and 17, the cutting member 222 may be advanced distally in an undeployed orientation a short distance along tracks 224 and 226 until the first pin 236 enters the distal portion 228 of the first track 224. The distal portion 228 may comprise a camming surface 252 which may cause the first pin 236 to be lifted toward junction point 230 as the cutting member 222 continues to be advanced distally. In result, the cutting member 222 is transitioned gradually from an undeployed orientation, as illustrated in FIG. 16, wherein the tissue cutting edge 234 is not exposed above top surface 218, to a deployed orientation, as illustrated in FIG. 17, wherein the tissue cutting edge 234 is exposed above top surface 218. Said another way, advancing the first pin 236 against the camming surface 252 may cause the cutting member 222 to move about an axis transverse to the longitudinal axis L-L resulting in deployment of the tissue cutting edge 234.

Referring again to FIGS. 16 and 17, as the cutting member 222 transitions from an undeployed orientation to a deployed orientation, as described above, the first pin 236 may enter the common track portion 232. In addition, the engagement portion 240 of the cutting member 222 may be released from mating engagement with the driving tip 250 and may enter into a mating engagement with the retraction hook 248 as illustrated in FIG. 17.

Figure 18:
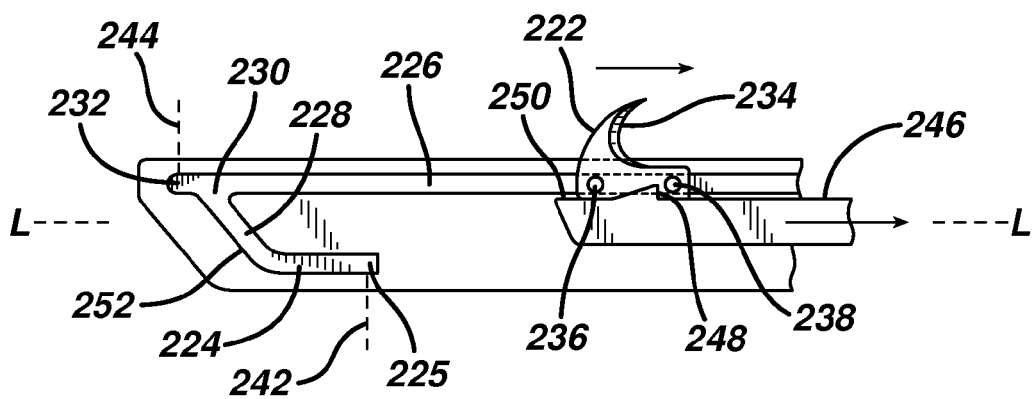
FIG. 18 is a partial cross-sectional view of the lower jaw of the end effector of the surgical cutting instrument of FIG. 12.

Referring now to FIGS. 17 and 18, the deployed cutting member 222 may then travel proximally from the distal ending position 244 in response to retraction motions by the driving member 246. As illustrated in FIG. 17, the tissue cutting edge 234 is proximally presented at the distal ending position 244. Retraction of the driving member 246 may cause the cutting member 222 to travel proximally along the longitudinal axis L-L. As the cutting member 222 begins to travel proximally, the first pin 236 rides in common track portion 232, and the second pin 238 rides in the second track 226. Upon reaching junction point 230, the first pin 236 is prevented from reentering the distal portion 228 of the first track 224 by driving member 246. Instead, the first pin 236 enters the second track 226. As illustrated in FIG. 18, both pins 236 and 238 may ride in the second track 226 for the remainder of the proximal travel of the cutting member 222.

In certain embodiments, the first jaw member 208 may comprise a slot (not shown) corresponding to slot 220 in the second jaw member 210. The slot of the first jaw member 208 may also extend along the longitudinal axis L-L, and may receive a top portion of the section of the deployed cutting member 222 exposed above top surface 218 during retraction of the cutting member 222 through slot 220.

Figure 19:
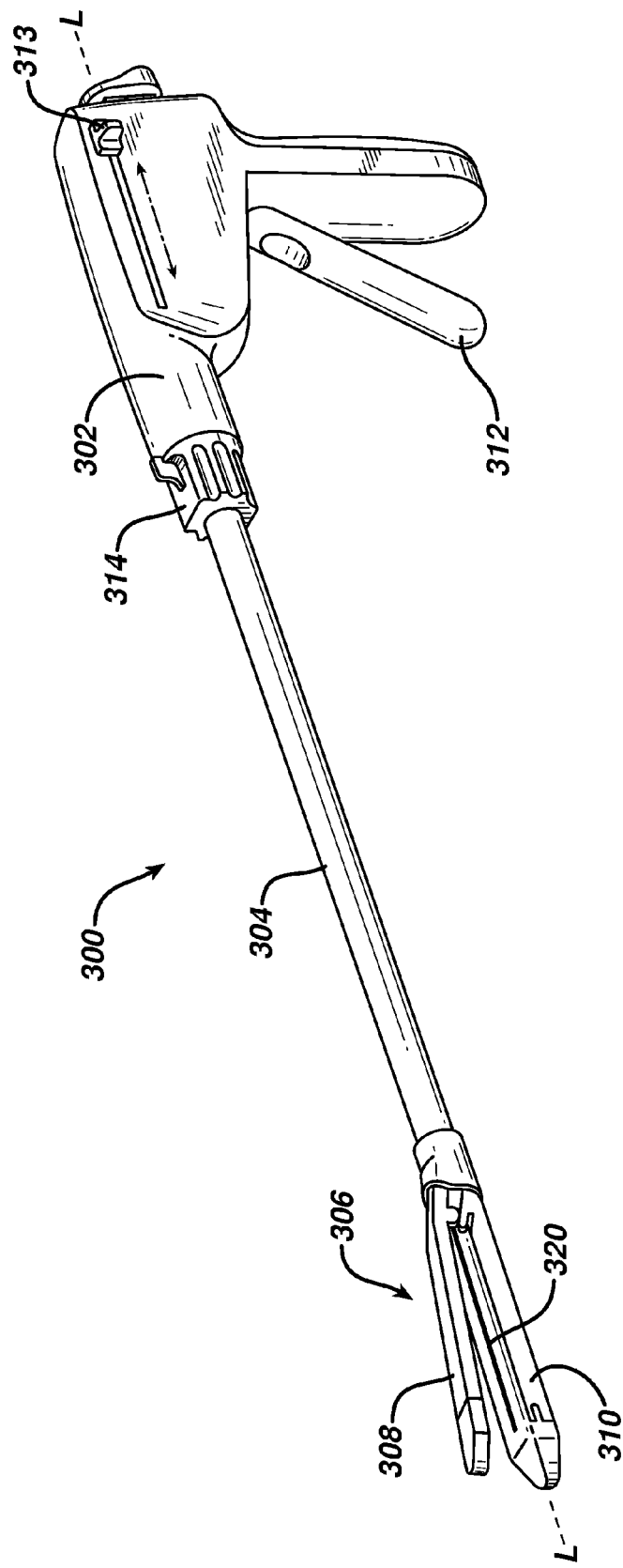
FIG. 19 is a prospective view of a surgical cutting instrument including a handle, a shaft and an end effector.

Referring to FIG. 19, a surgical instrument, generally 300, can comprise a handle 302, a shaft 304, and an end effector 306. In at least one embodiment, as shown in FIG. 19, the end effector 306 may comprise a first jaw member 308 and a second jaw member 310. The end effector 306 may be configured to perform surgical activities in response to firing motions applied thereto. The first jaw member 308 may be movable relative to the second jaw member 310 between a first position and a second position. The first position may be an open position and the second position may be a closed position. In at least one embodiment, referring to FIG. 19, the first jaw member 308 may be pivotally coupled to the second jaw member 310. Other suitable means for coupling the first jaw member 308 and the second jaw member 310 are contemplated within the scope of this disclosure.

Referring again to FIG. 19, the handle 302 may comprise a closure actuator 312, a firing actuator 313, and a rotation actuator 314. The closure actuator 312 may be pivotally coupled to handle 302. Actuation of the closure actuator 312 may cause the first jaw member 308 to move relative to the second jaw member 310. Rotating the rotation actuator 314 may result in rotation of the end effector 106 about a longitudinal axis L-L.

Figure 20:
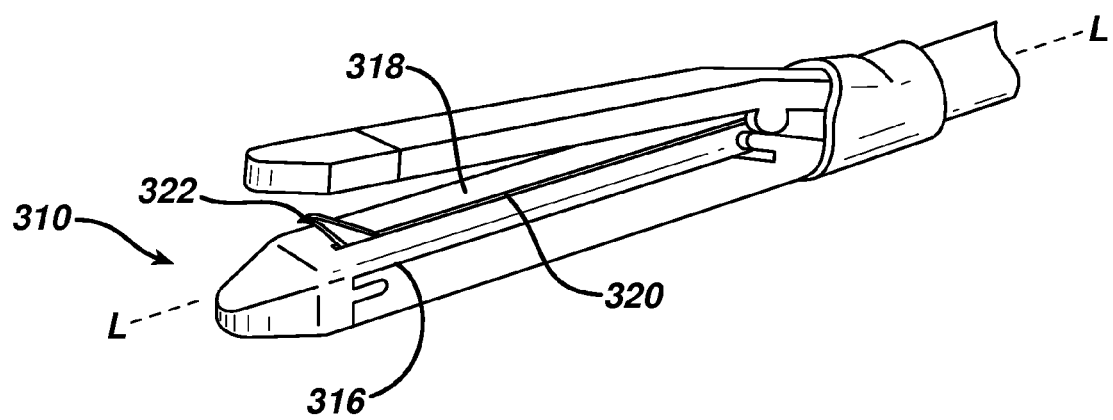
FIG. 20 is a prospective view of a lower jaw of the end effector of the surgical cutting instrument of FIG. 19 showing a deployed cutting member.
Figure 21:
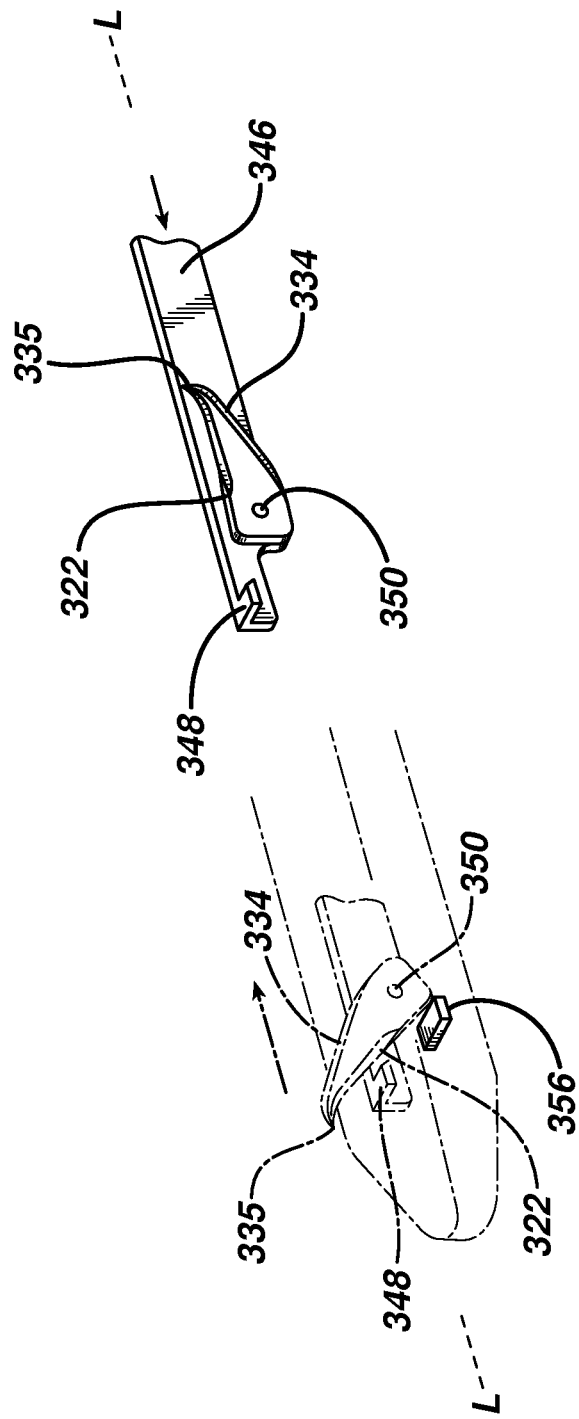
FIG. 21 includes two partial prospective views of a driving member of the surgical cutting instrument of FIG. 19, wherein the view in solid lines illustrates an undeployed cutting member, and the view in broken lines illustrates a deployed cutting member.

Referring to FIGS. 20-24, the second jaw member 310 may comprise a housing 316 including a top surface 318 having a slot 320 extending therethrough along the longitudinal axis L-L. As illustrated in FIG. 20, the housing 316 may include a cutting member 322 which may travel through slot 320 along the longitudinal axis L-L. The cutting member 322 may comprise a tissue cutting edge 334, and a piercing tip 335 at a distal portion of the cutting member as illustrated in FIG. 21.

Referring again to FIGS. 20-24, the surgical instrument 300 may further comprise a driving member 346, which may include a stop member 348 oriented at a distal portion thereof as illustrated in FIG. 21. The driving member 346 in the distal direction may be operably coupled, at a proximal portion thereof, to the firing actuator 313 such that an operator of the surgical instrument 300 may advance the driving member 346 distally by advancing the firing actuator 313 distally, and may retract the driving member 346 proximally by retracting firing actuator 313 proximally.

Referring to FIGS. 21-24, the cutting member 322 may be pivotally coupled to a distal portion of the driving member 346 proximal to stop member 348. For example, a pivot pin 350 can be used to couple the cutting member 322 to the driving member 346. Other means for coupling the cutting member 322 to the driving member 346 are contemplated within the scope of this disclosure. As illustrated in FIGS. 21-24, the cutting member 322 may pivot relative to the driving member 346 about an axis through pivot pin 350 and transverse to the longitudinal axis L-L. Pivoting the cutting member 322, in a counter clockwise direction, about pivot pin 350 may cause the cutting member 322 to transition from an undeployed orientation to a deployed orientation. In the undeployed orientation, the tissue cutting edge 334 and the piercing tip 335 of the cutting member 346 remain below the top surface 318 of the housing 316 as illustrated by the embodiment in solid lines in FIG. 21. In the fully deployed orientation, however, the tissue cutting edge 334 and the piercing tip 335 of the cutting member 346 are exposed above the top surface 318 of the housing 316 and the cutting member 346 rests against stop member 348 as illustrated by the embodiment in broken lines in FIG. 21.

Figure 22:
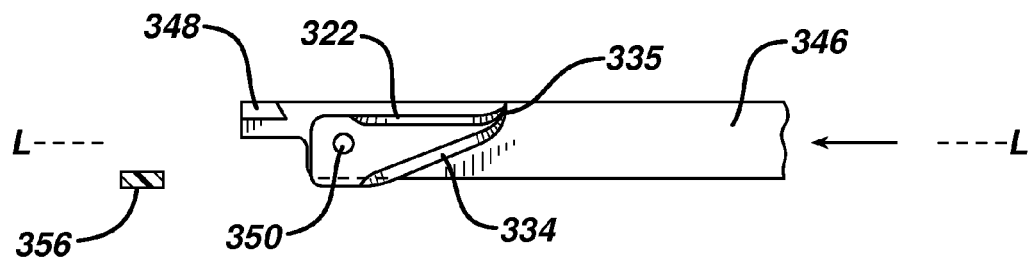
FIG. 22 is a partial cross-sectional view of a driving member of the surgical cutting instrument of FIG. 19.
Figure 23:
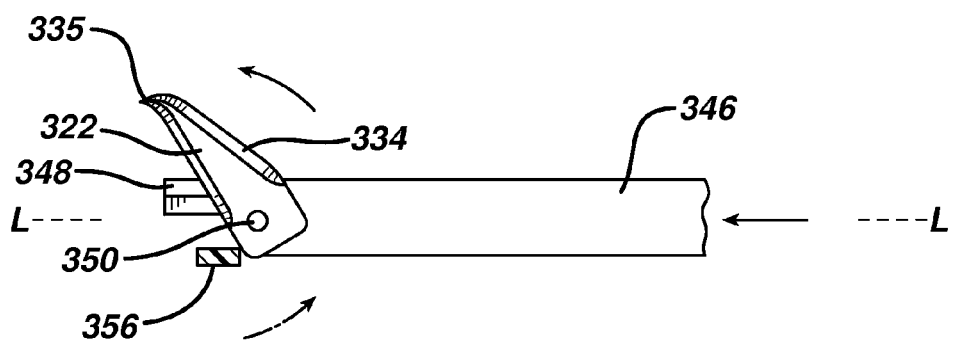
FIG. 23 is a partial cross-sectional view of a driving member of the surgical cutting instrument of FIG. 19.
Figure 24:
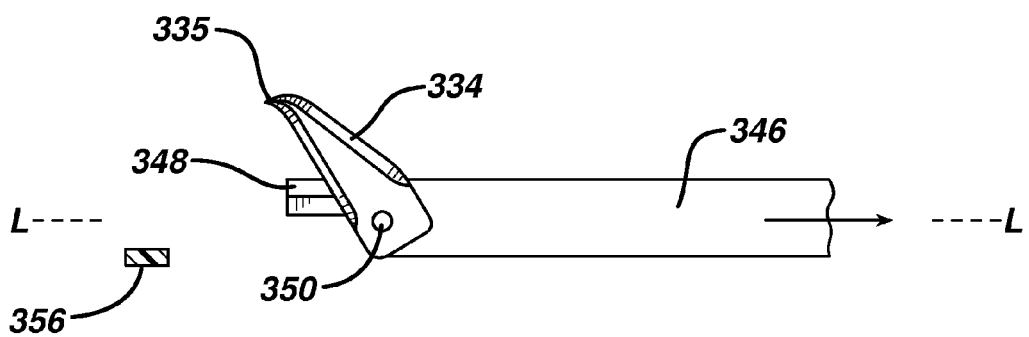
FIG. 24 is a partial cross-sectional view of a driving member of the surgical cutting instrument of FIG. 19.

Referring now to FIGS. 22-24, the housing 316 may comprise a deployment member 356. As illustrated in FIG. 22, the cutting member 322 can be advanced distally in an undeployed orientation by advancing the driving member 346 until the cutting member 322 engages the deployment member 356. Further advancing of the driving member 346 may cause the cutting member 322 to rotate counter clockwise about pivot pin 350 transitioning to a deployed orientation as illustrated in FIG. 23. Other deployment arrangements for deploying cutting member 322 are contemplated within the scope of the present disclosure.

The surgical instrument 300 can be used in performing a surgical tissue transection procedure. An operator may actuate the closure actuator 312 to grasp and secure the tissue to be transected between the first jaw member 308 and the second jaw member 310. The operator may then advance the cutting member 322 distally in an undeployed orientation, as described above, by advancing the firing actuator 313. Upon engaging the deployment member 356, the cutting member 322 may be rotated in a clockwise direction causing the piercing tip 335 to penetrate through tissue grasped between the jaw member 308 and 310. As the operator continues to advance the driving member 346, the cutting member 322 continues to rotate until the cutting member 322 is stopped by reaching the stop member 348. The operator may then retract the fully deployed cutting member 322 by retracting the firing actuator 313. The proximally presented tissue cutting edge 334 may cut through tissue grasped between jaw members 308 and 310 as the cutting member is retracted proximally. Transected tissue may then be released from end effector 306 by actuating the closure actuator 312 to open the jaw member 308 and 310.

Figure 25:
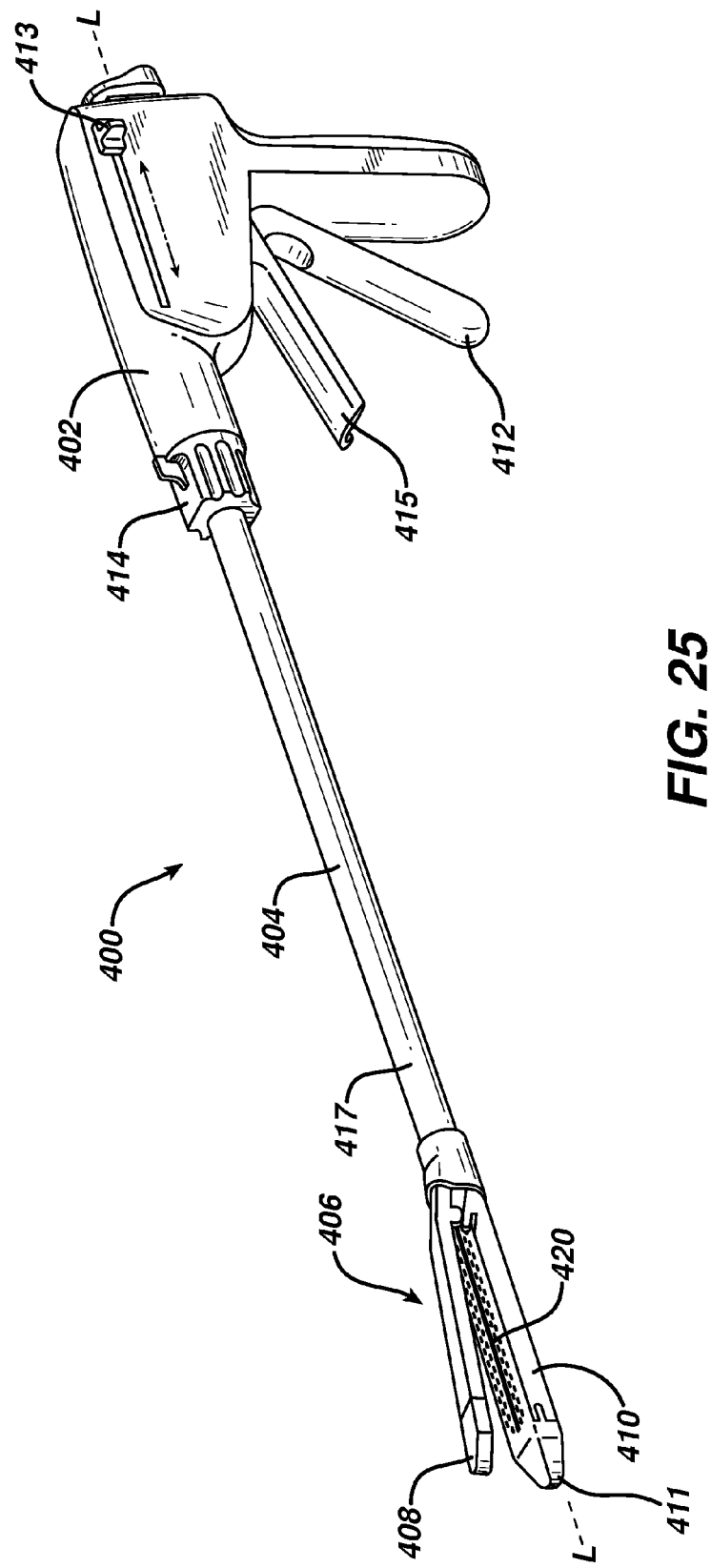
FIG. 25 is a prospective view of a surgical cutting and fastening instrument including a handle, a shaft and an end effector.

Referring to FIG. 25, a surgical fastening and cutting instrument, generally 400, can comprise a handle 402, a shaft 404, and an end effector 406. In at least one embodiment, as shown in FIG. 25, the end effector 406 may include a staple cartridge channel 410 for receiving a staple cartridge 411. The staple cartridge 411 can be configured to operably support surgical staples therein. End effector 406 can further include an anvil 408, which can be pivotally connected to staple cartridge channel 410 and can be pivoted between open and closed positions by an end effector closure system.

In order to deploy the staples from staple cartridge 411, surgical instrument 400 can further include a staple driver configured to traverse staple cartridge 411 and a firing drive configured to advance the staple driver within the staple cartridge. In various embodiments, anvil 408 can be configured to deform at least a portion of the staples as they are deployed from the staple cartridge. Several embodiments of end effector closure systems and firing drives are disclosed in U.S. Pat. No. 6,905,057, entitled SURGICAL STAPLING INSTRUMENT INCORPORATING A FIRING MECHANISM HAVING A LINKED RACK TRANSMISSION, which issued on Jun. 14, 2005, and U.S. Pat. No. 7,044,352, entitled SURGICAL STAPLING INSTRUMENT HAVING A SINGLE LOCKOUT MECHANISM FOR PREVENTION OF FIRING, which issued on May 16, 2006, the entire disclosures of each of these patents are incorporated by reference herein.

In various embodiments, a surgical instrument in accordance with the present invention can include a system for moving, or articulating, an end effector relative to an elongate shaft assembly of the surgical instrument. For example, surgical instrument 400 can include an articulation joint (not shown) which can movably connect end effector 406 and shaft 404. In various embodiments, the articulation joint can permit end effector 406 to be moved relative to shaft 404 in a single plane or, alternatively, multiple planes. In either event, the articulation joint can include one or more pivot axes about which end effector 406 can be articulated.

Surgical instrument 400 can further include a locking mechanism (not shown) which can fix, or lock, the relative relationship between end effector 406 and elongate shaft assembly 404. Locking mechanisms in accordance with the present disclosure are disclosed in U.S. Pat. No. 7,784,662, entitled SURGICAL INSTRUMENT WITH ARTICULATING SHAFT WITH SINGLE PIVOT CLOSURE AND DOUBLE PIVOT FRAME GROUND, which issued on Aug. 31, 2010, U.S. Pat. No. 7,455,208, entitled SURGICAL INSTRUMENT WITH ARTICULATING SHAFT WITH RIGID FIRING BAR SUPPORTS, which issued on Nov. 25, 2008, and U.S. Patent Application Publication No. 2007/0027469 A1, entitled SURGICAL STAPLING AND CUTTING DEVICE AND METHOD FOR USING THE DEVICE, which was filed on Jul. 24, 2006, the entire disclosures of which are each hereby incorporated by reference herein.

Referring to FIG. 25, the handle 402 may comprise a rotation actuator 414. Actuation of the rotation actuator 414 may result in rotation of the end effector 406 about a longitudinal axis L-L. The handle 402 may further comprise a closure actuator 412. The closure actuator 412 may be pivotally coupled to handle 402. Actuation of the closure actuator 412 may cause the anvil 408 to move relative to the cartridge channel 410. Handles and actuation mechanisms in accordance with the present disclosure are disclosed in U.S. Pat. No. 5,465,895, entitled SURGICAL STAPLER INSTRUMENT, which issued on Nov. 19, 1995, and U.S. patent application Ser. No. 12/830,013, entitled SURGICAL STAPLING INSTRUMENTS, which was filed on Jul. 2, 2010, the entire disclosures of which are each incorporated by reference herein. In an illustrative example, closure actuator 412 may be operably coupled to a closure tube 417. Actuation of the closure actuator 412 may cause the closure tube 417 to move distally. Distal movement of the closure tube 417 may effect pivotal movement of the anvil 408 toward the cartridge channel 410, which may effect tissue clamping.

Figure 26:
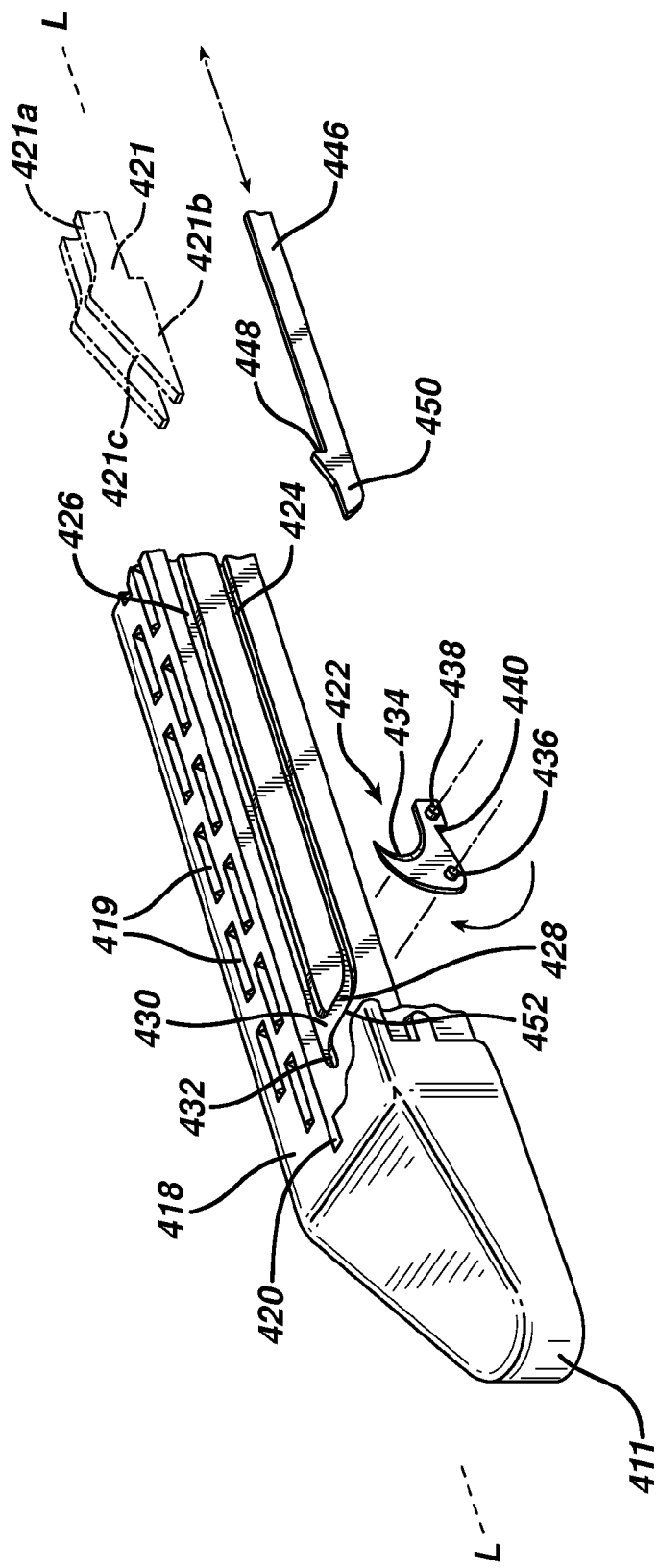
FIG. 26 is a partial exploded prospective view of a staple cartridge of the end effector of the surgical instrument of FIG. 25.
Figure 27:
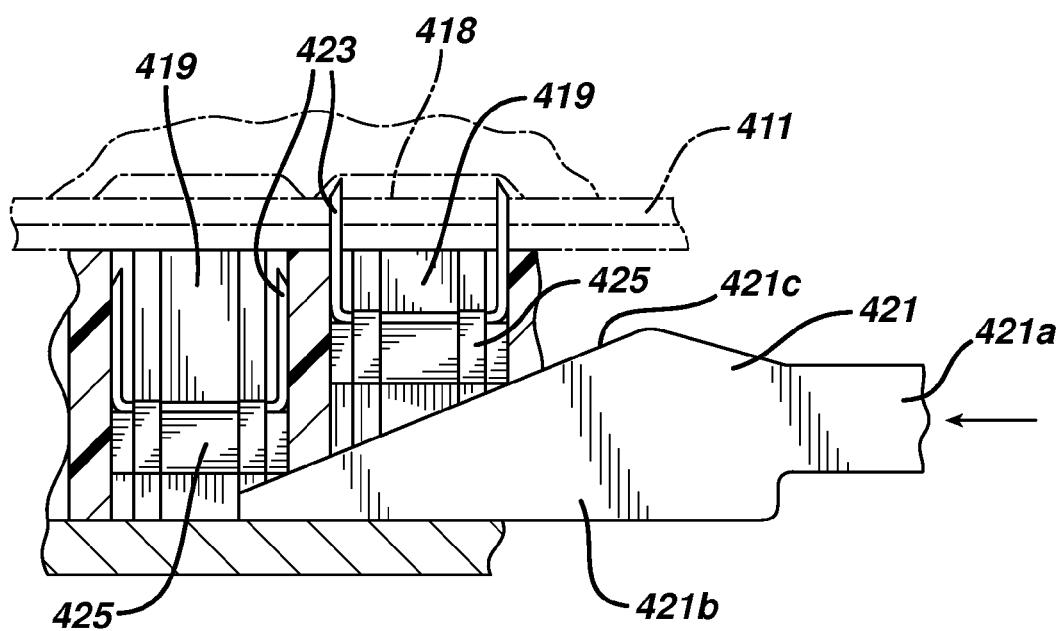
FIG. 27 is a partial cross-sectional view of the staple cartridge of FIG. 26, and a driving member of the surgical instrument of FIG. 25.

Referring to FIGS. 25-27, the handle 402 of the surgical cutting and fastening instrument 400 may further comprise a firing actuator 415 for deploying staples from staple cartridge 411. The staple cartridge 411 may be divided by a central elongated slot 420 as illustrated in FIG. 26. A plurality of staple receiving pockets 419 may be formed within the staple cartridge 411 and arranged in laterally spaced longitudinal rows. Staples 423 may be operably supported on corresponding drivers 425 that are movably positioned within the pockets 419 as illustrated in FIG. 27. The drivers 425 may be arranged in laterally spaced longitudinal rows. Drivers 425 may be slidably received within the pockets 419. Each driver 425 may support a single staple or plural staples 423 such that movement of the driver 425 through pocket 419 may deploy the staple or staples 423 as illustrated in FIG. 27.

The cartridge 411 may further include longitudinal slots (not shown) arranged to receive wedges 421 which are provided at a distal end of a firing driver arrangement (not shown) which in turn may be operably coupled to firing actuator 415 in handle 402. Actuation of firing actuator 415 may cause wedges 421 to move distally by moving the firing driver distally through shaft 404. Wedges 421 may be moved distally through the longitudinal slots within cartridge 411. Each wedge 421 may comprise an elongated portion 421a and a camming portion 421b. The camming portion 421b may include a single-angle upper cam surface 421c. Upon distal movement of the wedges 421, cam surfaces 421c can engage and push upward the drivers 425 in the staple cartridge 411 to effect the firing of the staples 423 toward the anvil 408. Various exemplary cartridge designs and firing driver arrangements in accordance with the present disclosure are disclosed in U.S. Pat. No. 5,465,895, entitled SURGICAL STAPLER INSTRUMENT, which issued Nov. 19, 1995, and U.S. Pat. No. 7,669,746, entitled STAPLE CARTRIDGES FOR FORMING STAPLES HAVING DIFFERING FORMED STAPLE HEIGHTS, which issued Mar. 2, 2010, the entire disclosures of which are each hereby incorporated by reference herein.

Referring again to FIGS. 25 and 26, the surgical cutting and fastening instrument 400 may further include a cutting member actuator 413, a driving member 446, and a cutting member 422. The cutting member 422 may travel through slot 420 along the longitudinal axis L-L. As illustrated in the exploded view in FIG. 26, the cartridge 411 may include a first track 424, and a second track 426. Tracks 424 and 426 may extend along the longitudinal axis L-L such that they are substantially parallel with each other. In addition, tracks 424 and 426 may extend in a plane that is substantially perpendicular to the top surface 418, wherein the second track 426 is closer to the top surface 418 than the first track 424. A distal portion 428 of the first track 424 may converge to intersect with the second track 426 at a junction point 430. Tracks 424 and 426 may further extend distally beyond junction point 430 forming a common track portion 432.

Figure 28:
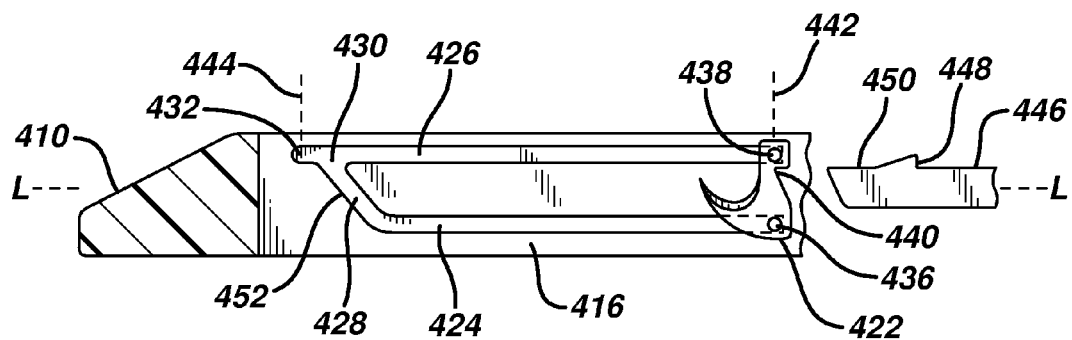
FIG. 28 is a partial cross-sectional view of the staple cartridge of FIG. 26 illustrating an undeployed cutting member.
Figure 29:
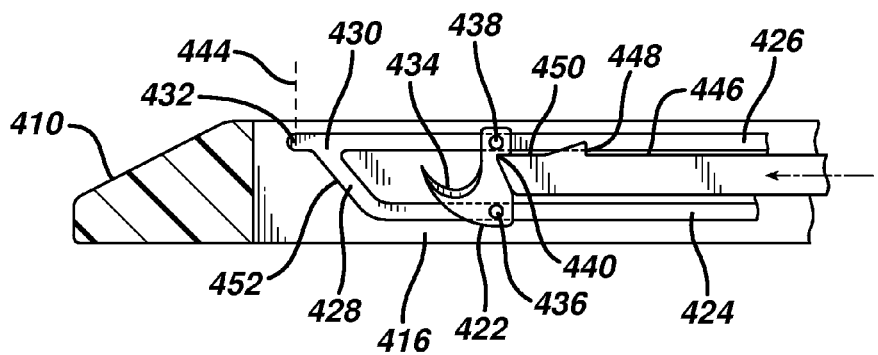
FIG. 29 is a partial cross-sectional view of the staple cartridge of FIG. 26 illustrating an undeployed cutting member.
Figure 30:
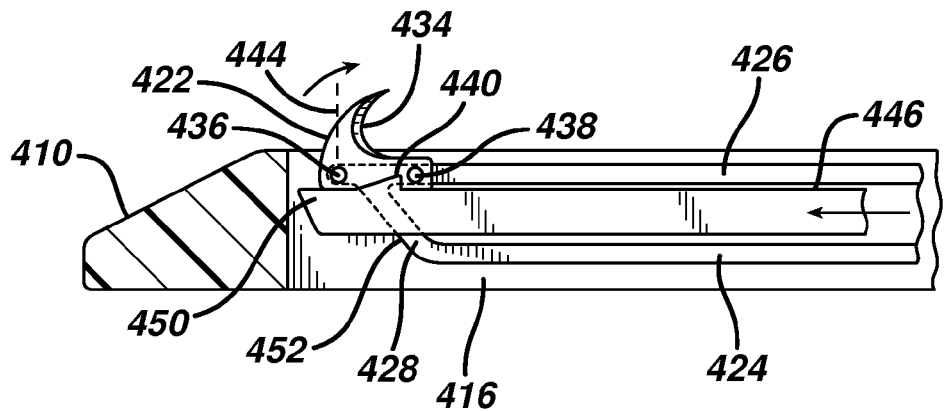
FIG. 30 is a partial cross-sectional view of the staple cartridge of FIG. 26 illustrating a deployed cutting member.

Referring to FIGS. 26, and 28-31, the cutting member 422 may include a tissue cutting edge 434, a first pin 436, a second pin 438, and an engagement portion 440. The cutting member 422 may travel between a proximal starting position 442 as illustrated in FIG. 28, and a distal ending position 444 as illustrated in FIG. 30. At the proximal starting position 442, the first pin 436 may ride in the first track 424, and the second pin 438 may ride in the second track 426, causing the cutting member 422 to remain in an undeployed orientation. In the undeployed orientation, as illustrated in FIG. 28, the tissue cutting edge 434 of the cutting member 422 is not exposed above the top surface 418.

As illustrated in the exploded view in FIG. 26, the driving member 446 may include a retraction hook 448 and a driving tip 450. The driving member 446 may be operably coupled, at a proximal portion thereof, to the cutting member actuator 413 such that an operator of the surgical instrument 400 may advance the driving member 446 distally by advancing the cutting member actuator 413 distally, and may retract the driving member 446 proximally by retracting cutting member actuator 413 proximally.

Referring to FIGS. 28 and 29, advancing the driving member 446 distally may bring the driving tip 450 into mating engagement with an engagement portion 440 of cutting member 422. With the first pin 436 riding in the first track 424, and the second pin 438 riding in the second track 426, further advancing of the driving member 446 may enable the cutting member 422 to travel distally from the proximal starting position 442 through slot 420 as illustrated in FIG. 29.

Referring to FIGS. 29 and 30, the cutting member 422 may be advanced distally in an undeployed orientation along tracks 424 and 426 until the first pin 436 enters the distal portion 428 of the first track 424. The distal portion 428 may comprise a camming surface 452 which may cause the first pin 436 to be lifted toward junction point 430 as the cutting member 422 continues to be advanced distally. In result, the cutting member 422 is transitioned gradually from an undeployed orientation, as illustrated in FIG. 29, wherein the tissue cutting edge 434 is not exposed above top surface 418, to a deployed orientation, as illustrated in FIG. 30, wherein the tissue cutting edge 434 is exposed above top surface 418. Said another way, advancing the first pin 436 against the camming surface 452 may cause the cutting member 422 to move about an axis transverse to the longitudinal axis L-L resulting in deployment of the cutting member 422.

Referring again to FIGS. 29 and 30, as the cutting member 422 transitions from an undeployed orientation to a deployed orientation, as described above, the first pin 436 enters the common track portion 432. In addition, the engagement portion 440 of the cutting member 422 is released from mating engagement with the driving tip 450 and enters into a mating engagement with the retraction hook 448 as illustrated in FIG. 30.

Figure 31:
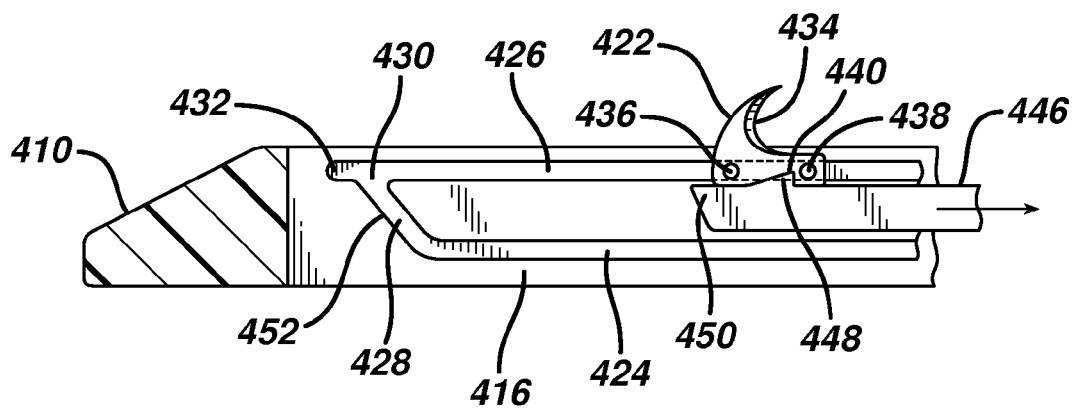
FIG. 31 is a partial cross-sectional view of the staple cartridge of FIG. 26 illustrating a deployed cutting member.
Figure 32:
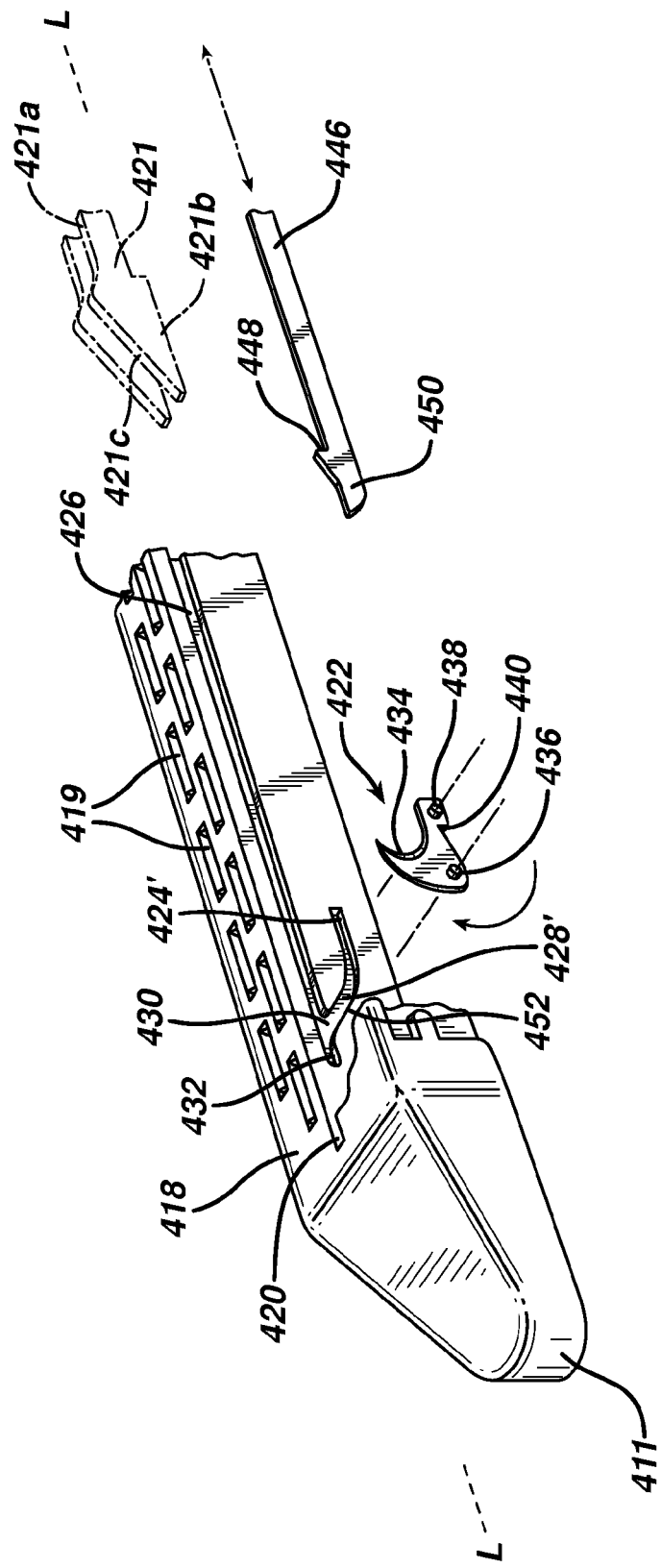
FIG. 32 is a partial exploded prospective view of a staple cartridge of the end effector of the surgical instrument of FIG. 25.

Referring now to FIGS. 30 and 31, the deployed cutting member 422 may then travel proximally from the distal ending position 444 to the proximal starting position 442 in response to retraction motions by the driving member 446. As illustrated in FIG. 30, the tissue cutting edge 434 is proximally presented at the distal ending position 444. Retraction of the driving member 446 may cause the cutting member 422 to travel proximally along the longitudinal axis L-L. As the cutting member begins to travel proximally, the first pin 436 rides in common track portion 432, and the second pin 438 rides in the second track 426. Upon reaching junction point 430, the first pin 436 is prevented from reentering the distal portion 428 of the first track 424 by driving member 446. Instead, the first pin 436 enters the second track 426. As illustrated in FIG. 31, both pins 436 and 438 may ride in the second track 426 for a remainder of the proximal travel of the cutting member 422.

In certain embodiments, the anvil 408 may comprise a slot (not shown) corresponding to slot 420 in the cartridge 411. The slot of anvil 408 may also extend along the longitudinal axis L-L, and may receive a top portion of the section of the deployed cutting member 422 exposed above top surface 418 during retraction of the cutting member 422 through slot 420.

In certain embodiments, wedges 421 may be operably coupled to move simultaneously with the driving member 446 such that a common actuating member (not shown) may simultaneously move wedges 421 and driving member 446. For example, during a first stroke of the common actuating member, wedges 421 may be advanced distally simultaneously with driving member 446 such that wedges 421 come in contact with drivers 425 as the driving tip 450 of the driving member 446 enters into mating engagement with the engagement portion 440 of the cutting member 422. During the remainder of the first stroke, the undeployed cutting member 422 may be advanced simultaneously with wedges 421 through staple cartridge 411 as staples 423 are deployed by wedges 421. At the end of the first stroke, the cutting member 422 may reach a fully deployed orientation with a proximally presented tissue cutting edge 434 at the distal ending position 444 as previously discussed and as illustrated in FIG. 30. During a second stroke of the common actuating member, the cutting member 422 may be retracted to cut through tissue now stapled with staples 423. Wedges 421 may be simultaneously retracted with cutting member 422.

The surgical instrument 400 can be used in performing a surgical tissue fastening and cutting procedure. An operator may actuate the closure actuator 412 of the handle 402 to grasp and secure tissue between the anvil 408 and the staple cartridge 411. The operator may then actuate the firing actuator 415 to deploy staples 423, as described in detail above. Once the staples 423 are fired into tissue, the operator may then advance the cutting member 422 distally in an undeployed orientation by advancing the cutting member actuator 413. Upon reaching the distal ending position 444, the cutting member 422 reaches a fully deployed orientation. The operator may then retract the fully deployed cutting member 422 by retracting the cutting member actuator 413. The proximally presented tissue cutting edge 434 may cut through tissue grasped between anvil 408 and cartridge 411 as the cutting member 422 is retracted proximally. Stapled transected tissue may then be released from end effector 406 by actuating the closure actuator 412 to open anvil 408.

Figure 33:
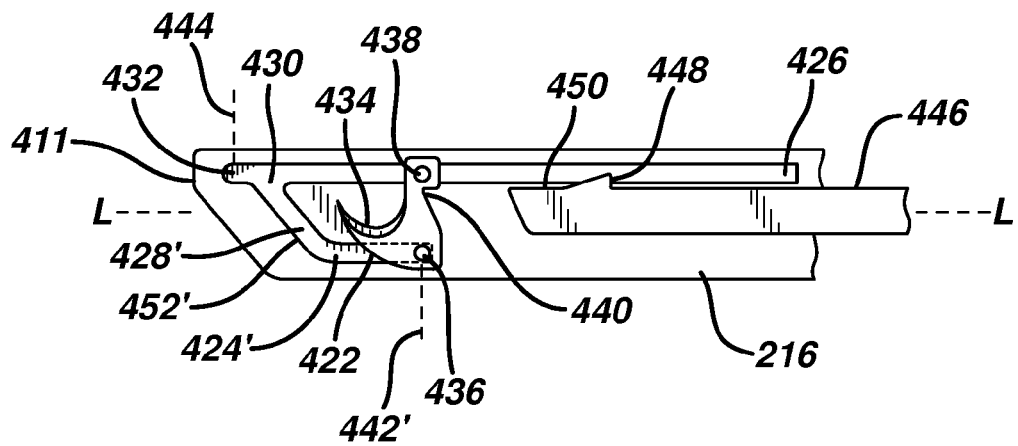
FIG. 33 is a partial cross-sectional view of the staple cartridge of FIG. 32 illustrating an undeployed cutting member.
Figure 34:
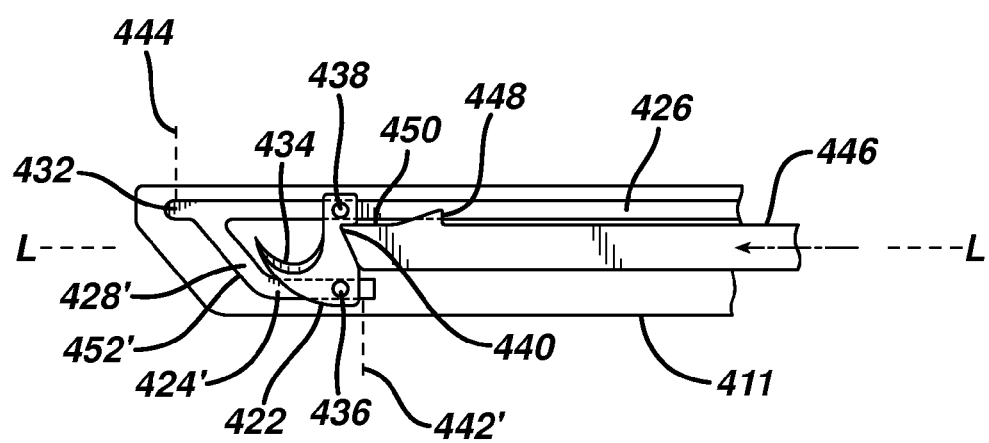
FIG. 34 is a partial cross-sectional view of the staple cartridge of FIG. 32 illustrating an undeployed cutting member.
Figure 35:
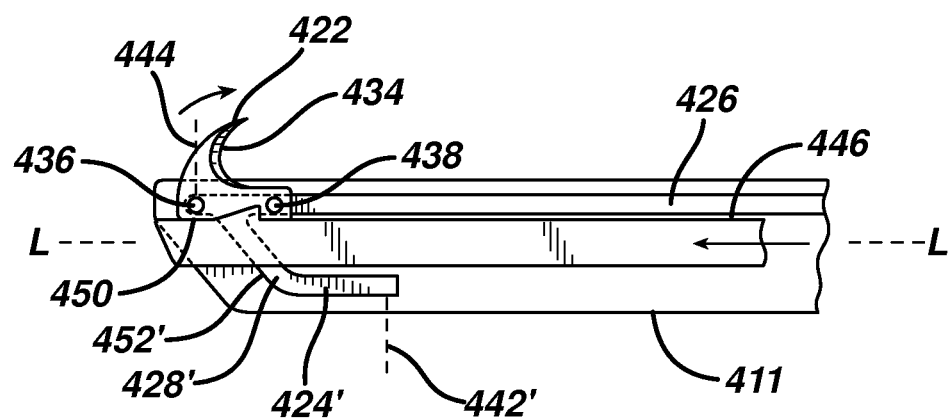
FIG. 35 is a partial cross-sectional view of the staple cartridge of FIG. 32 illustrating a deployed cutting member.

Referring to FIGS. 32-36, in an alternative embodiment, a first track 424' may replace the first track 424 of the staple cartridge 411. As illustrated in FIG. 33, the first track 424' may begin at a distal portion along the length of the staple cartridge 411. The cutting member 422 may travel from a proximal starting position 442' as illustrated in FIG. 33 to the distal ending position 444 as illustrated in FIG. 35. At the proximal starting position 442', the first pin 436 may ride in the first track 424', and the second pin 438 may ride in the second track 426, causing the cutting member 422 to remain in an undeployed orientation. As illustrated in FIG. 33, in an undeployed orientation, the tissue cutting edge 434 of the cutting member 422 is not exposed above the top surface 418.

Referring to FIGS. 33 and 34, advancing the driving member 446 distally may bring the driving tip 450 into mating engagement with engagement portion 440 of cutting member 422. With the first pin 436 riding in the first track 424', and the second pin 438 riding in the second track 426, further advancing of the driving member 446 may enable the cutting member 422 to travel a short distance distally from the proximal starting position 242' through slot 420 as illustrated in FIG. 34.

Referring to FIGS. 34 and 35, the cutting member 422 may be advanced distally in an undeployed orientation a short distance along tracks 424' and 426 until the first pin 436 enters a distal portion 428' of the first track 424'. The distal portion 428' may comprise a camming surface 452' which may cause the first pin 436 to be lifted toward junction point 430 as the cutting member 422 continues to be advanced distally. In result, the cutting member 422 is transitioned gradually from an undeployed orientation, as illustrated in FIG. 33, wherein the tissue cutting edge 434 is not exposed above top surface 418, to a deployed orientation, as illustrated in FIG. 35, wherein the tissue cutting edge 434 is exposed above top surface 418. Said another way, advancing the first pin 436 against the camming surface 452' may cause the cutting member 422 to move about an axis transverse to the longitudinal axis L-L resulting in deployment of the tissue cutting edge 434.

Referring again to FIG. 35, as the cutting member 422 transitions from an undeployed orientation to a deployed orientation, as described above, the first pin 436 enters the common track portion 432. In addition, the engagement portion 440 of the cutting member 422 is released from mating engagement with the driving tip 450 and enters into a mating engagement with the retraction hook 448 as illustrated in FIG. 35.

Figure 36:
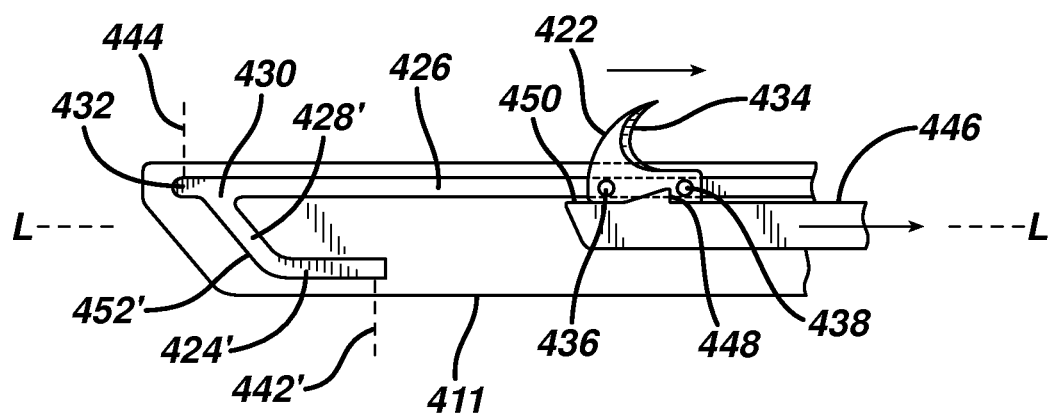
FIG. 36 is a partial cross-sectional view of the staple cartridge of FIG. 32 illustrating a deployed cutting member.

Referring now to FIGS. 35 and 36, the deployed cutting member 422 may then travel proximally from the distal ending position 444 in response to retraction motions by the driving member 446. As illustrated in FIG. 35, the tissue cutting edge 434 is proximally presented at the distal ending position 444. Retraction of the driving member 446 may cause the cutting member 422 to travel proximally along the longitudinal axis L-L. As the cutting member 422 begins to travel proximally, the first pin 436 rides in common track portion 432, and the second pin 438 rides in the second track 426. Upon reaching junction point 430, the first pin 436 is prevented from reentering the distal portion 428' of the first track 424' by driving member 446. Instead, the first pin 436 enters the second track 426. As illustrated in FIG. 36, both pins 436 and 438 may ride in the second track 426 for the remainder of the proximal travel of the cutting member 422.

Various embodiments are described and illustrated in this specification to provide an overall understanding of the elements, steps, and use of the disclosed device and methods. It is understood that the various embodiments described and illustrated in this specification are non-limiting and non-exhaustive. Thus, the invention is not limited by the description of the various non-limiting and non-exhaustive embodiments disclosed in this specification. In appropriate circumstances, the features and characteristics described in connection with various embodiments may be combined, modified, or reorganized with the steps, components, elements, features, aspects, characteristics, limitations, and the like of other embodiments. Such modifications and variations are intended to be included within the scope of this specification. As such, the claims may be amended to recite any elements, steps, limitations, features, and/or characteristics expressly or inherently described in, or otherwise expressly or inherently supported by, this specification. Further, Applicants reserve the right to amend the claims to affirmatively disclaim elements, steps, limitations, features, and/or characteristics that are present in the prior art regardless of whether such features are explicitly described herein. Therefore, any such amendments comply with the requirements of 35 U.S.C. §112, first paragraph, and 35 U.S.C. §132(a). The various embodiments disclosed and described in this specification can comprise, consist of, or consist essentially of the steps, limitations, features, and/or characteristics as variously described herein.

Any patent, publication, or other disclosure material identified herein is incorporated by reference into this specification in its entirety unless otherwise indicated, but only to the extent that the incorporated material does not conflict with existing definitions, statements, or other disclosure material expressly set forth in this specification. As such, and to the extent necessary, the express disclosure as set forth in this specification supersedes any conflicting material incorporated by reference herein. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

The devices disclosed herein can be designed to be disposed of after a single use, or they can be designed to be used multiple times. In either case, however, the device may be reconditioned for reuse after at least one use. Reconditioning can include a combination of the steps of disassembly of the device, followed by cleaning or replacement of particular pieces, and subsequent reassembly. In particular, the device may be disassembled, and any number of particular pieces or parts of the device can be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as ethylene oxide, steam, autoclaving, soaking in sterilization liquid, gamma radiation, x-rays, or higher energy electrons. The radiation kills bacteria on the instrument and in the container. The sterilized instrument can then be stored in the sterile container. The sealed container keeps the instrument sterile until it is opened in the medical facility.

The invention claimed is:

1. A surgical cutting instrument, comprising:
   a first jaw member;
   a second jaw member movably supported relative to the first jaw member for selective movement between an open position and a closed position to clamp tissue therebetween upon application of a closing motion thereto; and
   a cutting member comprising a tissue cutting edge to cut the tissue clamped between the first jaw member and the second jaw member upon application of a retraction motion to the cutting member, wherein the cutting member comprises an engagement portion configured for releasable engagement with an actuation member of the surgical cutting instrument.

2. The surgical cutting instrument of claim 1, wherein the cutting member is movable from an undeployed position to a deployed position.

3. The surgical cutting instrument of claim 2, wherein the cutting member is movable from the undeployed position to the deployed position by moving the cutting member about a deployment axis.

4. The surgical cutting instrument of claim 3, wherein the first jaw member defines a longitudinal axis, and wherein the deployment axis is transverse to the longitudinal axis.

5. The surgical cutting nstrument of claim 3, wherein the cutting member comprises a piercing tip configured to pierce through the tissue clamped between the first jaw member and the second jaw member upon the moving of the cutting member about the deployment axis.

6. A surgical cutting instrument, comprising:
   a first jaw member;
   a second jaw member movably supported relative to the first jaw member for selective movement between an open position and a closed position to clamp tissue therebetween upon application of a closing motion thereto; and
   a cutting member comprising a tissue cutting edge to cut the tissue clamped between the first jaw member and the second jaw member upon application of a retraction motion to the cutting member, wherein the cutting member is configured to be advanced distally in a stowed configuration from a first position to a second position along a length of the first jaw member.

7. A surgical staple cartridge assembly for use with a surgical stapler, the staple cartridge assembly comprising:
   a staple cartridge housing configured to be operably supported in the surgical stapler, wherein the staple cartridge housing comprises:
      a top surface;
      a slot; and
      at least one staple cavity; and
   a cutting member positioned within the staple cartridge housing, the cutting member comprising a tissue cutting edge configured to cut tissue, wherein the cutting member is proximally retractable through the slot upon application of a retraction motion thereto, wherein the tissue cutting edge is proximally presented as the cutting member is proximally retracted through the tissue, and wherein the cutting member comprises an engagement portion configured for releasable engagement with an actuating member of the surgical stapler.

8. The surgical staple cartridge assembly of claim 7, wherein the cutting member is movable from an undeployed position to a deployed position.

9. The surgical staple cartridge assembly of claim 8, wherein the cutting member is movable from the undeployed position to the deployed position by moving the cutting member about a deployment axis.

10. The surgical staple cartridge assembly of claim 8, wherein the cutting member comprises a piercing tip configured to pierce through the tissue upon moving the cutting member about the deployment axis.

11. A surgical staple cartridge assembly for use with a surgical stapler, the surgical staple cartridge assembly comprising:
    a staple cartridge housing configured to be operably supported in the surgical stapler, wherein the staple cartridge housing comprises:
       a top surface;
       a slot; and
       at least one staple cavity; and
    a cutting member positioned within the staple cartridge housing, the cutting member comprising a tissue cutting edge configured to cut tissue, wherein the cutting member is proximally retractable through the slot upon application of a retraction motion thereto, wherein the tissue cutting edge is proximally presented as the cutting member is proximally retracted through the tissue, and wherein the cutting member is advanced distally without exposing the tissue cutting edge of the cutting member above the top surface of the staple cartridge housing.

12. A surgical cutting and fastening instrument, comprising:
    an elongate shaft;
    an elongate channel operably coupled to the elongate shaft and configured to operably support a staple cartridge therein;
    an anvil movably supported relative to the elongate channel for selective movement between an open position and a closed position, wherein tissue is clamped between the anvil and the staple cartridge supported within the elongate channel in response to opening and closing motions applied thereto from the elongate shaft; and
    a cutting member comprising a tissue cutting edge, wherein the cutting member is retractable relative to the elongate channel, wherein the tissue cutting edge is configured to cut tissue clamped between the anvil and the staple cartridge during retraction of the cutting member, and wherein the cutting member comprises an engagement portion configured for releasable engagement with an actuating member of the surgical cutting and fastening instrument.

13. The surgical cutting and fastening instrument of claim 12, wherein the cutting member is movable from an undeployed position to a deployed position.

14. The surgical cutting and fastening instrument of claim 13, wherein the cutting member is movable from the undeployed position to the deployed position by moving the cutting member about a deployment axis.

15. The surgical cutting and fastening instrument of claim 14, wherein the cutting member comprises a piercing tip configured to pierce through the tissue clamped between the anvil and the staple cartridge upon moving the cutting member about the deployment axis.

16. A surgical cutting and fastening instrument, comprising:
   an elongate shaft;
   an elongate channel operably coupled to the elongate shaft and configured to operably support a staple cartridge therein;
   an anvil movably supported relative to the elongate channel for selective movement between an open position and a closed position, wherein tissue is clamped between the anvil and a staple cartridge supported within the elongate channel in response to opening and closing motions applied thereto from the elongate shaft; and
   a cutting member comprising a tissue cutting edge, wherein the cutting member is retractable relative to the elongate channel, wherein the tissue cutting edge is configured to cut tissue clamped between the anvil and the staple cartridge during retraction of the cutting member, and wherein the cutting member is advanced distally without exposing the tissue cutting edge of the cutting member above a top surface of a staple cartridge housing.

17. A surgical cutting and fastening instrument, comprising:
   a first jaw having a housing, the housing including a top surface;
   a second jaw movably supported relative to the first jaw upon application of opening and closing motions thereto; and
   a cutting member including a tissue cutting edge, the cutting member being movable from a proximal starting position to a distal ending position upon application of a firing motion thereto, and from the distal ending position to the proximal starting position upon application of a retraction motion thereto, the cutting member being further movably supported within the housing of the first jaw such that when the cutting member moves from the proximal starting position to the distal ending position, the tissue cutting edge is positioned below the top surface of the housing of the first jaw, and when the cutting member moves from the distal ending position to the proximal starting position, the tissue cutting edge extends above the top surface of the housing of the first jaw.

18. A surgical staple cartridge, comprising:
   a cartridge housing including a top surface, the cartridge housing operably supporting a plurality of surgical staples therein; and
   a cutting member movably supported within the cartridge housing and including a tissue cutting edge, the cutting member being movable from a proximal starting position to a distal ending position, and from the distal ending position to the proximal starting position, the cutting member further being movably supported within the cartridge housing such that when the cutting member moves from the proximal starting position to the distal ending position, the tissue cutting edge is positioned below the top surface and when the cutting member moves from the distal ending position to the proximal starting position, the tissue cutting edge extends above the top surface.

* * * * *